United States Patent
Guerry et al.

(10) Patent No.: US 11,339,148 B2
(45) Date of Patent: May 24, 2022

(54) **CRYSTALLINE FORMS OF THE CXCR7 RECEPTOR ANTAGONIST (3S,4S)-1-CYCLOPROPYLMETHYL-4-{[5-(2,4-DIFLUORO-PHENYL)-ISOXAZOLE-3-CARBONYL]-AMINO}-PIPERIDINE-3-CARBOXYLIC ACID (1-PYRIMIDIN-2-YL-CYCLOPROPYL)-AMIDE

(71) Applicant: IDORSIA PHARMACEUTICALS LTD., Allschwil (CH)

(72) Inventors: Philippe Guerry, Allschwil (CH); Markus Von Raumer, Allschwil (CH)

(73) Assignee: IDORSIA PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 16/964,885

(22) PCT Filed: Jan. 25, 2019

(86) PCT No.: PCT/EP2019/051819
§ 371 (c)(1),
(2) Date: Jul. 24, 2020

(87) PCT Pub. No.: WO2019/145460
PCT Pub. Date: Jan. 8, 2019

(65) Prior Publication Data
US 2021/0115033 A1 Apr. 22, 2021

(30) Foreign Application Priority Data
Jan. 26, 2018 (WO) .................. PCT/EP2018/051938

(51) Int. Cl.
*C07D 413/14* (2006.01)
(52) U.S. Cl.
CPC ........ *C07D 413/14* (2013.01); *C07B 2200/13* (2013.01)
(58) Field of Classification Search
CPC .................................................. C07D 413/14
See application file for complete search history.

(56) References Cited

U.S. PATENT DOCUMENTS

2014/0154179 A1  6/2014  Fan et al.

FOREIGN PATENT DOCUMENTS

| WO | 2004050024 A2 | 6/2004 |
|---|---|---|
| WO | 2005026149 A1 | 3/2005 |
| WO | 2005032490 A3 | 7/2005 |
| WO | 2006087543 A1 | 8/2006 |
| WO | 2012168315 A1 | 12/2012 |
| WO | 2013084241 A1 | 6/2013 |
| WO | 2013190508 A3 | 3/2014 |
| WO | 2014191929 A1 | 12/2014 |
| WO | 2015033299 A1 | 3/2015 |
| WO | 2015034820 A1 | 3/2015 |
| WO | 2015044900 A1 | 4/2015 |
| WO | 2016040515 A1 | 3/2016 |
| WO | 2016087370 A1 | 6/2016 |
| WO | 2018019929 A1 | 2/2018 |

OTHER PUBLICATIONS

Adlere et al. Mol Pharmacol 96:737-752. (Year: 2019).*
International Search Report received in Application No. PCT/EP2019/051819 dated Feb. 28, 2019, 2 pages.
Written Opinion of the International Searching Authority received in Application No. PCT/EP2019/051819 dated ___, 7 pages.
Antonelli A et al.; Thyroid. 2013, 23(11):1461-9.
Armengol MP et al.; J Immunol. 2003, 170(12):6320-8.
Azab AK et al.; Blood. 2014, 124(12):1905-14.
Banisadr G et al.; J Neuroimmune Pharmacol. 2016; 11(1):26-35.
Bao J et al.; Biochem Biophys Res Commun. 2016; 469(1):1-7.
Basarab GS et al.; J. Med. Chem 2014, 57(14), 6060-6082.
Berahovich RD et al.; Immunology. 2014, 141(1):111-22.
Biajoux V et al.; J Transl Med. 2012, 18; 10:251.
Blades MC et al.; Arthritis Rheum. Mar. 2002; 46(3):824-36.
Brunn A et al.; Neuropathol Appl Neurobiol. 2013, 39(7):772-87.
Calatozzolo C et al.; Cancer Biol Ther. 2011, 11(2), 1-12.
Cao Z et al.; Nat Med. 2016,; 22(2):154-62.
Cecchi L et al.; Eur. J. Org. Chem. 2006, 4852-4860.
Chang HC et al.; Immunology. 2017, 154, 274-284 (DOI: 10.1111/imm.12881).
Chen D et al.; Sci Rep. 2015, 5:16813.
Chen N et al.; Tumour boil. 2016, 37(1):567-75.
Chen SC et al.; Arch Dermatol Res. 2010, 302(2):113-23.
Chu T et al., Neuroscientist. 2017, 23(6): 627-648.
Cruz-Orengo L et al.; J Exp Med. 2011, 14; 208(2):327-39.
Cruz-Orengo L et al.; J Neuroinflammation. 2011, 6; 8:170.
De-Min M et al.; World J Surg Oncol. 2016, 14(1):256-266.
Ding BS et al.; Nature. 2014, 505(7481):97-102.
Domanska UM et al.; European J of cancer. 2013, 49(1):219-30.
Douglas SD et al.; J Leukoc Biol. 2017; 102: 1155-1157.
Duda DG et al.; Clin Cancer Res; 2011, 17(8); 2074-80.
Ebsworth et al.; Neuro Oncol (2013) 15 (suppl 3):iii37-iii61. ET-023.
Ebsworth K et al.; J Clin Oncol. 2012, 30(15) e13580.
European Pharmacopeia Technical Guide (1999, p. 86).
Feig C et al, PNAS 2013, 110(50), 20212-7.
Gasparik V et al.; ACS Med Chem Lett. Jan. 12, 2012; 3(1):10-4.
Goguet-Surmenian et al.; Br J Cancer. 2013, 109(6):1579-85.
Gottle P et al.; Ann Neurol. 2010, 68(6):915-24.
Grymula K et al.; Int J cancer. 2010, 127(11):2554-68.
Guillemot et al.; Br J Cancer. 2012, 107(12):1944-9.
Hartmann TN et al.; J Leukoc Biol. 2008,; 84(4):1130-40.
Hattermann et al.; Cancer research 2010, 70 (8):3299-3308.

(Continued)

*Primary Examiner* — Erich A Leeser
(74) *Attorney, Agent, or Firm* — Jeff B. Vockrodt; Culhane Meadow, LLP

(57) ABSTRACT

The invention relates to crystalline forms of (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide; processes for the preparation thereof, pharmaceutical compositions containing such crystalline forms, pharmaceutical compositions prepared from such crystalline forms, and their use as a medicament, especially as CXCR7 receptor modulators.

32 Claims, 2 Drawing Sheets

(56) References Cited

OTHER PUBLICATIONS

Hattermann et al.; Oncol Rep. 2012, 27: 1348-1352.
Heinrich EL et al.; J Transl Med. 2012, 10:68.
Huguet F et al, ChemMedChem 2012, 7, 1020-1030.
Ikeda Y et al.; Cell. 2013, 5; 155(6):1323-36.
Iwakiri S et al.; Cancer. 2009, 115(11):2580-93.
Jin Z et al.; Int J Cancer. 2009, 125(9):2229-35.
Johan Wouters and Luc Quéré; Pharmaceutical Salts and Co-crystals, 2012 (10 pages).
Lewellis SW et al.; J Cell Biol. 2013, 4; 200(3):337-55.
Liberman J et al.; Plos One. 2012, 7(8):e43665.
Linder J et al.; Journal of the American Chemical Society, 2011, 133(4), 1044-1051.
Liu et al., Mol Med Rep. 2016, 13(4):3604-12.
Liu H et al.; Plos One. 2012, 7(4):e34608.
Liu L et al.; Mol Med Rep. 2013, 8(1):140-6.
Liu SC et al.; Neuro-Oncology 2014; 16(1):21-28).
Liu Y; Anticancer Res. 2015, 35(1):53-64.
Liu Z et al.; World J Surg Oncol. 2014, 12:348.
Long P et al.; Tumour biol. 2016, 37(6):7473-80.
Lu J et al.; Exp Mol Pathol. 2016, 100(1):184-91.
Lukacs NW et al.; Am J Pathol. 2002, 160(4):1353-60.
Ma W. et al.; Biochem Pharmacol. 2014, 1; 89(1):99-108.
Maussang D et al.; J biol Chem. 2013, 288(41):29562-72.
McCandless EE et al.; Am J Pathol. 2008, 172(3):799-808.
McConnell AT et al.; Br J Dermatol. 2016, doi: 10.1111/bjd.14720 (27 pages).
Miao et al., PNAS 2007, 104(40):15735-15740.
Mikami S et al.; J Pharmacol Exp Ther. 2008, 327(2):383-92.
Monnier J et al.; Eur J Cancer. 2012, 48(1):138-48.
Nanki T et al.; J Immunol. 2000, 165(11):6590-8.
Naumann et al.; Plos One. 2010, 5(2) e9175.
Ngamsri KC et al.; J Immunol. 2017, 198(6):2403-2413.
P. Heinrich Stahl, Camille G. Wermuth; Handbook of Pharmaceutical Salts. Properties, Selection and Use., 2008.
Patadia M et al.; Am J Rhinol Allergy. 2010, 24(1):11-6.
Petty JM et al.; J Immunol. 2007, 178(12):8148-57.
Phillips RJ et al.; J Clin Invest. 2004, 114(3):438-46.
Porter JC et al.; J Immunol. 2008, 180(3):1866-77.
Rafii S et al.; Nat Cell Biol. 2015, 17(2):123-36.
Raggo C et al.; Cancer Res. 2005, 65(12):5084-95.
Rankin SM et al.; Immunol lett. 2012, 145(1-2):47-54.
Remington, The Science and Practice of Pharmacy, 21st Edition (2005), Part 5, "Pharmaceutical Manufacturing" (5 pages).
Rupertus K et al.; Clin Exp Metastasis. 2014, 31(4):447-59.
Salmaggi et al.; Cancer Biol Ther.2009, 8:17, 1-7.
Sanchez-Martin et al.; Trends Mol Med. 2013, 19(1):12-22.
Sartina E et al.; Pediatr Res. 2012, 71(6):682-8.
Shakir M et al.; Pancreas. 2015, 44(4):528-34.
Sit SY et al.; Bioorganic & Medicinal Chemistry Letters, 20 (2010), 1272-1277.
T.W. Greene, P.G.M. Wuts; "Protective Groups in Organic Synthesis", 1999.
Teicher BA et al.; Clin Can Res. 2010, 16(11):2927-31.
Thomas MN et a.; Transpl Int. 2015, 28(12):1426-35.
Ueno et al.; Rheumatol Int. 2005, 25(5):361-7.
Villalvilla A et al.; Expert Opin Ther Targets. 2014, 18(9):1077-87.
Virani S et al.; Am J Reprod Immunol 2013, 70:386-397.
Walters MJ et al.; Br J Cancer. 2014, 110(5):1179-88.
Wang A et al.; J Immunol. 2009, 182(7):4448-58.
Wang et al., Journal of Biochemical Chemistry, 2008, 293(7):4283-4294.
Wang HX et al.; Mol Clin Oncol. 2015, 3(6):1229-1232.
Watanabe K et al.; Arthritis Rheum. 2010, 62(11):3211-20.
Werner L et al.; J Leukoc Biol. 2011, 90(3):583-90.
Werner L et al.; Theranostics. 2013, 3(1):40-6.
Williams JL et al.; J Exp Med. 2014, 5; 211(5):791-9.
Xia XM et al.; PLoS One. 2011, 6(11):e27282.
Xue TC et al.; Exp Ther Med. 2012, 3(1):117-123.
Zeng LF et al.; Bioorganic & Medicinal Chemistry Letters 18 (2008), 4521-4524.
Zgraggen S et al.; PLoS One. 2014, 9(4):e93665.
Zhang H et al.; Tumour biol. 2016, 37(2):2415-23.
Zhang Y et al.; Oncol Rep. 2014, 32(3):965-72.
Zhao D et al.; Biochemistry. 2015, 17; 54(45):6806-14.
Zheng et al., Journal of Experimental and Clinical Cancer Research, 2010, 29:31.
Zheng K et al.; J Exp Clin Cancer Res. 2010, 29:31.
Zhou SM et al.; Oncol Rep. 2016, 35(6):3453-9.
Zhu X et al.; Int J Oncol. 2016, 48(6):2321-9.
Zohar Y et al.; J Clin Invest. 2014, 124(5):2009-22.
Burns et al., Journal of Experimental Medicine, 2006, 203(9):2201-2213.
Ed. R. Hilfiker, VCH, 2006), Chapter 8: U.J. Griesser: The Importance of Solvates).
Gellman S et al. ; Eur. J. Org. Chem. 2003, 721.
Koelink PJ et al.; Pharmacol Ther. 2012, 133(1):1-18.
Konrad FM et al.; Cell Death Dis. 2017, 8 (5).
Kryczek I et al.; Cancer Res. 2005, 65(2):465-72.
Kumar R et al.; Cell Immunol. 2012, 272(2):230-41.
Liu Z et al.; J Surg Res. 2014, 191(2):379-88.
Sun et al.; Cancer Metastasis Rev. 2010, 29(4), 709-722.

\* cited by examiner

CRYSTALLINE FORMS OF THE CXCR7 RECEPTOR ANTAGONIST (3S,4S)-1-CYCLOPROPYLMETHYL-4-{[5-(2,4-DIFLUORO-PHENYL)-ISOXAZOLE-3-CARBONYL]-AMINO}-PIPERIDINE-3-CARBOXYLIC ACID (1-PYRIMIDIN-2-YL-CYCLOPROPYL)-AMIDE

CROSS REFERENCE TO RELATED APPLICATIONS

This application is a filing under 35 U.S.C. § 371 of international application number PCT/EP2019/051819, filed Jan. 25, 2019, which claims priority to application number PCT/EP2018/051938 filed on Jan. 26, 2018, the entire disclosures of each of which are hereby incorporated by reference.

The present invention relates to novel crystalline forms (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide (hereinafter also referred to as "COMPOUND"):

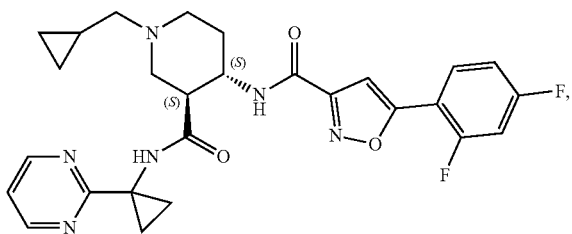

processes for the preparation thereof, pharmaceutical compositions comprising said crystalline forms, pharmaceutical compositions prepared from such crystalline forms, and their use as modulators of the CXCL11/CXCL12 receptor CXCR7, especially for the treatment of cancer, autoimmune disorders, inflammatory diseases, transplant rejection, or fibrosis. The invention further relates to said crystalline forms as pharmaceuticals in combination with one or more therapeutic agents and/or radiotherapy and/or targeted therapy in the treatment of cancers (especially brain tumors including malignant gliomas, glioblastoma multiforme; neuroblastoma; pancreatic cancer including pancreatic adenocarcinoma/pancreatic ductal adenocarcinoma; gastro-intestinal cancers including colon carcinoma, hepatocellular carcinoma, gastric cancer; Kaposi's sarcoma; leukemias including adult T-cell leukemia; lymphoma; lung cancer; breast cancer; rhabdomyosarcoma; prostate cancer; esophageal squamous cancer; oral squamous cell carcinoma; endometrial cancer; thyroid carcinoma including papillary thyroid carcinoma; metastatic cancers; lung metastasis; skin cancer including melanoma and metastatic melanoma; bladder cancer; multiple myelomas; osteosarcoma; head and neck cancer; and renal carcinomas including renal clear cell carcinoma, metastatic renal clear cell carcinoma).

Chemokine receptors are a group of G-protein coupled receptors (GPCRs) that bind peptidic chemokine ligands with high affinity. The predominant function of chemokine receptors is to guide leukocyte trafficking to lymphoid organs and tissues under resting conditions as well as during inflammation, but a role for certain chemokine receptors on non-hematopoietic cells and their progenitors has also been recognized.

CXCR7 (alias ACKR3, alias RDC1, alias CMKOR1, alias GPR159) has two known chemokine ligands: CXCL12 (alias stromal cell-derived factor 1, SDF-1; alias Pre-B cell growth stimulating factor, PBSF) and CXCL11 (alias I-TAC, alias INF-y-inducible T cell a chemo-attractant).

CXCL12, a stroma-derived chemo-attractant participates in the immune surveillance and in the regulation of inflammatory responses. CXCL12 is secreted by bone marrow stromal cells, endothelial cells, heart, skeletal muscle, liver, brain, kidney, parenchymal cells and play an essential role in stem cell proliferation, survival, and homing of hematopoietic/progenitor to the bone marrow (Rankin S M et al.; Immunol let. 2012, 145(1-2):47-54). CXCL12 also recruits bone-marrow derived progenitor cells to sites of vasculature formation. Moreover, it plays a prominent role in carcinogenesis. CXCL12 promotes the recruitment of endothelial progenitor cells and of myeloid derived suppressor cells to the tumor sites as well as other bone marrow derived cells. Furthermore, CXCL12 regulates angiogenesis/vasculogenesis linked to tumor progression and plays a key role in seeding circulating tumor cells to metastatic sites. Besides its chemotactic functions, CXCL12 has been shown to regulate tumor cell proliferation, motility and survival (Kryczek I et al.; Cancer Res. 2005, 65(2):465-72; Teicher B A et al.; Clin Can Res. 2010, 16(11):2927-31; Domanska U M et al.; European J of Cancer. 2013, 49(1):219-30).

In addition to CXCR7, CXCL12 binds and activates CXCR4 (alias Fusin, alias Leukocyte-derived seven-trans-membrane-domain receptor; LESTR, alias D2S201E, alias seven-transmembrane-segment receptor, alias HM89, alias lipopolysaccharide-associated protein 3; lap3, alias LPS-associated protein 3) while CXCL11 binds and activate CXCR3 (alias GPR9, alias CD183).

The interaction of CXCR7 and its ligands CXCL12 and CXCL11 (henceforth referred to as the CXCR7 axis) is thus involved in guiding receptor bearing cells to specific locations in the body, particularly to sites of inflammation, immune injury and immune dysfunction and is also associated with tissue damage, the induction of apoptosis, cell growth and angiostasis. CXCR7 and its ligands are upregulated and highly expressed in diverse pathological situations including cancer, autoimmune disorders, inflammation, infection, transplant rejection, fibrosis and neurodegeneration.

Cancers figure among the leading causes of death worldwide. Tumors are comprised of abnormally proliferating malignant cancer cells but also of a functionally supportive microenvironment. This tumor microenvironment is comprised of a complex array of cells, extracellular matrix components, and signaling molecules and is established by the altered communication between stromal and tumor cells. As tumors expand in size, they elicit the production of diverse factors that can help the tumor to grow such as angiogenic factors (promoting ingrowth of blood vessels) or that can help to evade the attack of the host immune response. CXCL12 is such an angiogenic and immunomodulatory factor produced in tumors.

The present crystalline CXCR7 modulators may be useful, alone, or in combination in cancers where the expression of the CXCL11/CXCL12 receptor CXCR7 correlates with disease progression in cancer (among others in pancreas cancer, pancreatic adenocarcinoma, breast cancer, hormone refractory prostate cancer, renal cell carcinoma, cervical cancer, cervical intra-epithelial neoplasia, papillary thyroid carcinoma, bladder cancer, Ewing's sarcoma, colon cancer, colorectal cancers, lung cancer, lung adenocarcinoma, non-small cell lung cancer, meningiomas, MALT lymphoma, cutaneous squamous cell carcinoma, neuro-endocrine tumors, nasopharyngal carcinoma, glioblastoma multiforme, astrocytomas, gliomas, hepatocellular carcinoma, oestrogen positive breast cancer, osteosarcoma, gallbladder cancer, kidney tumors, and renal cell carcinoma). CXCR7 is also expressed in leukemias, adenocarcinomas, brain metastases, multiple myelomas, head and neck cancer, primary cutaneous melanoma, melanoma, metastatic melanoma, rhabdomyosarcoma, pituitaty adenoma, oral squamous cell carcinoma, oral tumors, lymphoplasmacytic lymphoma, adult T-cell leukemia, brain tumors, esophageal squamous cancer, esophageal cancer, ovarian carcinoma, lymphoma, viral-induced tumors, otorhinolaryngologic neoplasm, Burkitt's lymphoma, Hodgkin's lymphoma, thyroid cancers, cervical squamous cell carcinoma, endometrial cancer, neuroblastoma, gastro-intestinal cancer, lymphoproliferative disease, extramammary paget disease, acute myeloid leukemia, acute lymphoid leukemia, gastric cancer, nerve sheath tumors and choriocarcinoma, malignant pleural mesothelioma, neurilemnoma, meningioma, diffuse large B cell lymphoma, oral leukoplakia, Kaposi sarcoma, and alveolar rhabdomyosarcoma (for review see Sun et al.; Cancer Metastasis Rev. 2010, 29(4), 709-722).

The present CXCR7 modulators may be useful, alone, or in combination, in diseases where CXCR7 modulation using siRNA, shRNA, microRNAs, overexpression, CXCR7 knock-out animals, CXCR7 agonists, CXCR7 antagonists, antibodies or nanobodies have been shown to alter tumor growth in experimental disease models as single agents, or in combination with cytotoxic therapies in including among others hepatocellular carcinoma (Xue T C et al.; Exp Ther Med. 2012, 3(1):117-123; Zheng et al.; Journal of Experimental and Clinical Cancer Research. 2010, 11; 29:31), Kaposi's sarcoma (Raggo C et al.; Cancer Res. 2005, 65(12):5084-95), T cell leukemia (Jin Z et al.; Int J Cancer. 2009, 125(9):2229-35), lymphoma (Burns J M et al.; J Exp Med. 2006, 203(9):2201-13), lung carcinomas, breast cancer (Miao Z et al.; PNAS. 2007, 104(40):15735-40), gastric cancer (De-Min M et al.; World J Surg Oncol. 2016, 14(1):256-266), rhabdomyosarcoma (Grymula K et al.; Int J cancer. 2010, 127(11):2554-68), prostate cancer (Wang J et al.; J Biol Chem. 2008, 283(7):4283-94), pancreatic cancer (Shakir M et al.; Pancreas. 2015, 44(4):528-34), esophageal squamous cancer (Zhou S M et al.; Oncol Rep. 2016, 35(6):3453-9), endometrial cancer (Long P et al.; Tumour boil. 2016, 37(6):7473-80), papillary thyroid carcinoma (Zhang H et al.; Tumour boil. 2016, 37(2):2415-23), oral squamous cell carcinoma (Chen N et al.; Tumour boil. 2016, 37(1):567-75), lung metastasis (Goguet-Surmenian et al.; Br J Cancer. 2013, 109(6):1579-85), melanoma (McConnell A T et al.; Br J Dermatol. 2016, doi: 10.1111/bjd.14720), bladder cancer (Liu L et al.; Mol Med Rep. 2013, 8(1):140-6), multiple myeloma (Azab A K et al.; Blood. 2014, 124(12):1905-14), osteosarcoma (Zhang Y et al.; Oncol Rep. 2014, 32(3):965-72), colon cancer (Wang H X et al.; Mol Clin Oncol. 2015, 3(6):1229-1232), grade IV astrocytomas (Walters M J et al.; Br J Cancer. 2014, 110(5):1179-88), head and neck cancers (Maussang D et al.; J Biol Chem. 2013, 288(41):29562-72), neuroblastoma (Liberman J et al.; Plos One. 2012, 7(8):e43665) and glioblastoma (Liu Y; Anticancer Res. 2015, 35(1):53-64; Walters M J et al.; Br J Cancer. 2014, 110(5):1179-88; Ebsworth K et al.; J Clin Oncol. 2012, 30(15) e13580); to alter tumor-associated blood vessels (Miao Z et al.; PNAS. 2007, 104(40):15735-40); and to reduce tumor cell seeding (Grymula K et al.; Int J cancer. 2010, 127(11):2554-68).

The present CXCR7 modulators may be useful, alone, or in combination, in diseases where CXCR7 modulation (e.g. using siRNA, shRNA, microRNAs, overexpression, CXCR7 knock-out animals, CXCR7 agonists, CXCR7 antagonists, antibodies or nanobodies) has been shown to regulate leucocyte migration (Berahovich R D et al.; Immunology. 2014, 141(1):111-22) and to promote myelin/neuronal repair (Williams J L et al.; J Exp Med. 2014, 5; 211(5):791-9; Gottle P et al.; Ann Neurol. 2010, 68(6):915-24), providing beneficial effects in experimental disease models of inflammatory, autoimmune and demyelinating diseases, including multiple sclerosis and autoimmune encephalomyelitis (Cruz-Orengo L et al.; J Neuroinflammation. 2011, 6; 8:170; Bao J et al.; Biochem Biophys Res Commun. 2016 Jan. 1; 469(1):1-7), Guillain-Barré syndrome or autoimmune neuritis (Brunn A et al.; Neuropathol Appl Neurobiol. 2013, 39(7):772-87), rheumatoid arthritis (Watanabe K et al.; Arthritis Rheum. 2010, 62(11):3211-20), acute pulmonary inflammation/acute lung injury (Ngamsri K C et al.; J Immunol. 2017, 198(6):2403-2413; Petty J M et al.; J Immunol. 2007, 178(12):8148-57), asthma (Gasparik V et al.; ACS Med Chem Lett. 2012 Jan. 12; 3(1):10-4; Chang H C et al.; Immunology. 2017 DOI: 10.1111/imm.12881); to attenuate chronic hypoxia-induced pulmonary hypertension (Sartina E et al.; Pediatr Res. 2012, 71(6):682-8); lung fibrosis (Cao Z et al.; Nat Med. 2016; 22(2):154-62); and atherosclerosis (Zhao D et al.; Biochemistry. 2015, 17; 54(45):6806-14; Ma W. et al.; Biochem Pharmacol. 2014, 1; 89(1):99-108).

Furthermore, CXCR7 has been proposed to be involved in cardiac stem cell migration (Chen D et al.; Sci Rep. 2015, 5:16813), chronic allograft vasculopathy (Thomas M N et a.; Transpl Int. 2015, 28(12):1426-35), inflammatory bowel disease (Werner L et al.; Theranostics. 2013, 3(1):40-6), chronic rhinosinusitis (Patadia M et al.; Am J Rhinol Allergy. 2010, 24(1):11-6), human pulmonary vascular diseases (Rafii S et al.; Nat Cell Biol. 2015, 17(2):123-36), and development of severe preeclampsia (Lu J et al.; Exp Mol Pathol. 2016, 100(1):184-91); and to improve beneficial effects of mesenchymal stem cells based therapies for renal ischemia/reperfusion injury (Liu H et al.; Plos One. 2012, 7(4):e34608) and to induce anxiolytic-like behaviour (Ikeda Y et al.; Cell. 2013, 5; 155(6):1323-36). In addition to the above mentioned diseases CXCR7 modulators may be useful in the treatment of renal allograft rejection, systemic lupus erythematosus, osteoarthritis, pulmonary vascular diseases, acute renal failure, ischemia including cerebral ischemia, chronic allograft rejection, acute coronary syndrome, injured central nervous system; hyperlipidemia, HSCs transplantation, hypertension, pulmonary hypertension, Shiga-toxin-associated heomolytic uremic syndrome, HIV/AIDS; cirrhosis, stress-related disorders, proliferative diabetic retinopathy, West Nile virus encephalitis, vascular injury, pulmonary fibrosis, endometriosis, autoimmune thyroiditis, choroidal neovascularization-associated diseases, aplastic anemia, Sjögren's disease and vitiligo.

Mechanistically, recent studies have provided increasing evidence that activation of the CXCL12 pathway is a potential mechanism of tumor resistance to both conventional therapies and biological agents via multiple complementary actions: (i) by directly promoting cancer cell survival, invasion, and the cancer stem and/or tumor-initiating cell phenotype; (ii) by recruiting "distal stroma" (i.e., myeloid bone marrow-derived cells) to facilitate immune-suppression, tumor recurrence, and metastasis; and (iii) by promoting angiogenesis directly or in a paracrine manner (Duda D G et al: CXCL12 (SDF1alpha)-CXCR4/CXCR7 pathway inhibition: an emerging sensitizer for anticancer therapies?; Clin Cancer Res; 2011, 17(8); 2074-80) recently discussed preclinical and clinical data that support the potential use of anti-CXCL12 agents including CXCR7 modulators as sensitizers to currently available therapies in cancer treatments. In addition, the enhancement in CXCR7 expression on endothelium seems to be critical for the inflammatory infiltration in autoimmune diseases. CXCL12 and CXCL11 are key ligands in inflammatory immune response: (i) by acting on cell migration, on cell adhesion and cell survival (Kumar R et al.; Cell Immunol. 2012, 272(2):230-41); (ii) by driving differentiation, maturation and polarization of cell i.e., macrophages (Ma W. et al.; Biochem Pharmacol. 2014, 1; 89(1):99-108), CD4+ T cells (Zohar Y et al.; J Clin Invest. 2014, 124(5):2009-22), oligodendrocytes progenitors (Gottle P et al.; Ann Neurol. 2010, 68(6):915-24); (iii) by participating in homing processes (Lewellis S W et al.; J Cell Biol. 2013, 4; 200(3): 337-55). Therefore, targeting CXCR7 and thus regulating the level of its ligands would have a decisive role in the pathogenesis of a wide variety of autoimmune and inflammatory diseases. Sanchez-Martin et al (Trends Mol Med. 2013, 19(1):12-22) recently discussed dysregulation of CXCR7 in disease and highlighted the fact that this receptor is an attractive therapeutic target for the treatment of auto-immune diseases and inflammation.

Thus, the present CXCR7 antagonists may be useful, alone, or in combination with with one or more therapeutic agents and/or chemotherapy and/or radiotherapy and/or immunotherapy; in particular in combination with chemotherapy, radiotherapy, EGFR inhibitors, aromatase inhibitors, immunotherapy such as especially PD1 and/or PDL1 blockade and/or CTLA4 blockade, or other targeted therapies; for the prevention/prophylaxis or treatment of cancers such as carcinomas; adenocarcinomas; neuroendocrine tumors; skin cancer including melanoma and metastatic melanoma; lung cancer including non-small cell lung cancer; metastatic cancer; lung metastasis; bladder cancer including urinary bladder cancer; urothelial cell carcinoma; renal carcinomas including renal cell carcinoma; metastatic renal cell carcinoma, metastatic renal clear cell carcinoma; gastro-intestinal cancers including colon carcinoma, colorectal adenoma, colorectal adenocarcinoma, colorectal cancer, metastatic colorectal cancer, familial adenomatous polyposis (FAP), oesophageal cancer, oral squamous cell carcinoma; gastric cancer, gallbladder cancer, cholangiocarcinoma, hepatocellular carcinoma; pancreatic cancer such as pancreatic adenocarcinoma or pancreatic ductal (adeno) carcinoma; endometrial cancer; ovarian cancer; cervical cancer; neuroblastoma; prostate cancer including castrate-resistant prostate cancer; brain tumors including brain metastases, malignant gliomas, glioblastoma multiforme, medulloblastoma, meningiomas; breast cancer including triple negative breast carcinoma; oral tumors; nasopharyngeal tumors; thoracic cancer; head and neck cancer; leukemias including acute myeloid leukemia, adult T-cell leukemia; thyroid carcinoma including papillary thyroid carcinoma; choriocarcinoma; Ewing's sarcoma; osteosarcoma; rhabdomyosarcoma; Kaposi's sarcoma; lymphoma including Burkitt's lymphoma, Hodgkin's lymphoma, MALT lymphoma; primary intra-ocular B-Cell lymphoma, multiple myelomas and virally induced tumors; and diseases involving CXCR7 and/or CXCL12 and/or CXCL11 mediated metastasis, chemotaxis, cell adhesion, trans-endothelial migration, cell proliferation and/or survival.

Specifically, the potential role of CXCR7 in brain tumors, malignant glioma and in glioblastoma multiforme is known from the literature. Modulators of the CXCL12 pathway including CXCR7 modulators have been mentioned as potential therapeutic agents for treating brain cancer in combination with chemotherapeutic agents or radiotherapy. For example, Hattermann et al (Cancer research 2010, 70 (8):3299-3308) teach that CXCL12 "stimulation prevented camptothecin- and temozolomide-induced apoptosis and that a CXCR7 antagonist reduced the antiapoptotic effect of CXCL12". The authors concluded that "CXCR7 is a functional receptor for CXCL12 in astrocytomas/glioblastomas and mediates resistance to drug-induced apoptosis". Furthermore, Hattermann et al (Oncol Rep. 2012, 27: 1348-1352) teach that "CXCL12 abrogates the antiproliferative effect of temozolomide". The authors also teach that this effect could be almost completely abolished by a CXCR7 specific antagonist, "indicating that the anti-apoptotic effect of CXCL12 is mainly mediated via CXCR7". Ebsworth et al (Neuro Oncol (2013) 15 (suppl 3):iii37-iii61. ET-023) teach that a CXCR7 antagonist significantly prolongs survival when administered in combination with radiotherapy in a rat model of glioblastoma. This finding is supported by other studies (e.g. Ebsworth K et al.; J Clin Oncol. 2012, 30(15) e13580; Walters M J et al.; Br J Cancer. 2014, 110(5):1179-88) disclosing that in vivo inhibition of CXCR7 in concert with radiotherapy results in a significant extension of survival time in another rat model of glioblastoma. In addition, Liu S C et al (Neuro-Oncology 2014; 16(1):21-28) teach that inhibition of CXCL12 after irradiation inhibits tumor recurrence in autochtonous brain tumors in rats. Liu S C et al (Neuro Oncol. 2013, 16(1):21-8) also teach that inhibition of CXCL12 in a brain metastasis model after irradiation produced a marked inhibition of tumor growth and prolongation of lifespan compared to irradiation alone. Calatozzolo C et al (Cancer Biol Ther. 2011, 11(2), 1-12) teach in in vitro experiments that CXCR7 antagonists showed complete inhibition of glioma proliferation.

Specifically, a role for CXCR7 in pancreas tumors, has been described in the literature. Shakir et al. (Pancreas. 2015, 44(4):528-34) observed that CXCR4 and CXCR7, upon interaction with CXCL12, activate downstream protein kinases that promote a more aggressive behaviour. Moreover, the expression of CXCR7 and CXCl12 correlates with tumor histological grades (Liu Z et al.; World J Surg Oncol. 2014, 12:348). These findings were confirmed by Heinrich E L et al. (J Transl Med. 2012, 10:68). Therefore, CXCR7 modulators may be useful in the treatment of pancreas cancers.

CXCR7 modulators may also be useful in the treatment of papillary thyroid carcinoma. Liu Z et al. (J Surg Res. 2014, 191(2):379-88) described that CXCR7 messenger RNA and protein levels were markedly increased in papillary thyroid carcinoma and correlated with tumor progression. CXCR7 could regulate proliferation, cell cycle, apoptosis, invasion, and the expression of cell cycle regulatory proteins involved in the S-G2 phase transition. Knockdown of CXCR7 in papillary thyroid carcinoma cells suppressed cell proliferation and invasion, induced S phase arrest, and promoted apoptosis. Zhang H et al (Tumor Biol. 2016, 37(2):2415-23) further demonstrated that CXCR7 affects the growth of papillary thyroid carcinoma cells and participates in the tumorigenesis of papillary thyroid carcinoma, probably through regulating angiogenesis by the proangiogenic VEGF or IL-8. The expression and function of the CXCR7 axis in thyroid cancer was confirmed by Zhu X et al. (Int J Oncol. 2016, 48(6):2321-9)

CXCR7 modulators may also be useful in the treatment of lung cancer: Using a combination of overexpression and RNA interference, Miao Z et al (PNAS. 2007, 104(40): 15735-40) established that CXCR7 promotes growth of tumors formed from breast and lung cancer cells and enhances experimental lung metastases. Iwakiri S et al. (Iwakiri S et al.; Cancer. 2009, 115(11):2580-93) observed that higher expression of CXCR7 is linked to early and metastatic recurrence in pathological stage I non small cell lung cancer.

CXCR7 modulators may also be useful in the treatment of hepatocellular carcinoma: it was reported that CXCR7 expression is increased in hepatocellular carcinoma tissues. Knockdown of CXCR7 expression significantly inhibited hepatocellular carcinoma cells invasion, adhesion and angiogenesis. In addition, down-regulation of CXCR7 expression lead to a reduction of tumor growth in a xenograft model of hepatocellular carcinoma (Zheng K et al.; J Exp Clin Cancer Res. 2010, 29:31). Monnier J et al. (Eur J Cancer. 2012, 48(1):138-48) also observed in a cohort of 408 human hepatocellular carcinoma, that CXCR7 was significantly higher in tumours compared to normal liver controls. Immunohistochemical staining on human hepatocellular carcinoma sections confirmed that CXCR7 expression was much higher in cancer tissues. Using RNAi of CXCR7 in an hepatocellular carcinoma cell line, Xue T C et all (Exp Ther Med. 2012, 3(1):117-123) observed that CXCR7 downregulation decreased the growth of tumors and the number of lung metastases in nude mice. Moreover, tissue microarray showed that HCCs with high expression of CXCR7 were prone to metastasize to the lung. Downregulation of CXCR7 inhibits the growth and lung metastasis of human hepatocellular carcinoma cells with highly metastatic potential.

CXCR7 modulators may also be useful in the treatment of metastatic colon cancer: Guillemot et al. (Br J Cancer. 2012, 107(12):1944-9) observed that following injection of colorectal cancer cells, mice treated with a CXCR7 antagonists exhibited a significant reduction in lung metastasis. Wang H X et al (Mol Clin Oncol. 2015, 3(6):1229-1232) studied CXCR7 expression in colon cancer specimen and observed that CXCR7 levels were significantly higher in colon tumors compared with those in normal colon tissue. In addition, lymph node metastatic colon tumors exhibited significantly higher CXCR7 expression compared with non-metastatic tumors.

CXCR7 is also reported to be expressed in brain metastases (Salmaggi et al.; Cancer Biol Ther.2009, 8:17, 1-7). The authors concluded that the CXCL12/CXCR4/CXCR7 pathway could be an interesting target for further researches investigating the role of these molecules in invasion and proliferation of metastatic cells.

Specifically, the impact of CXCR7 on inflammatory demyelinating diseases is known from the literature. CXCR7 is expressed in various regions throughout the adult mouse brain and its expression is upregulated in mouse model for multiple sclerosis (Banisadr G et al.; J Neuroimmune Pharmacol. 2016 March; 11(1):26-35). Altered expression patterns of CXCL12 at the blood-brain barrier (BBB) is involved in multiple sclerosis and correlate with severity of the disease (McCandless E E et al.; Am J Pathol. 2008, 172(3):799-808). CXCR7 antagonism have been shown to be effective in experimental autoimmune encephalomyelitis in mice. Those recent studies strongly implicate CXCR7 as a disease-modifying molecule in multiple sclerosis via complementary mechanisms: (i) by facilitating leucocytes entry into the perivascular space via CXCL12 redistribution at the BBB (Cruz-Orengo L et al.; J Neuroinflammation. 2011, 6; 8:170; Cruz-Orengo L et al.; J Exp Med. 2011, 14; 208(2):327-39) and regulating the CXCR4-mediated activation of integrins (Hartmann T N et al.; J Leukoc Biol. 2008; 84(4):1130-40) (ii) by direct effect on microglial chemotaxis (Bao J et al.; Biochem Biophys Res Commun. 2016 Jan. 1; 469(1):1-7) and on inflammatory monocytes, facilitating their entry into the brain (Douglas S D et al.; J Leukoc Biol. 2017; 102: 1155-1157) (iii) by promoting remyelination via increase levels of CXCL12 enhancing CXCR4-mediated oligodendrocytes progenitor cells maturation (Williams J L et al.; J Exp Med. 2014, 5; 211(5):791-9; Gottle P et al.; Ann Neurol. 2010, 68(6):915-24). Recently, Chu et al (Neuroscientist. 2017, 23(6): 627-648) reviewed the importance of targeting the axis CXCL12/CXCR4/CXCR7 for demyelinating diseases, due to their central role in promoting the migration, proliferation and differentiation of oligodendrocytes progenitor cells. Thus, CXCR7 antagonism could therapeutically prevent inflammation and enhance myelin repair in the demyelinated adult CNS.

Specifically, the potential role of CXCR7 in rheumatoid arthritis is known from the literature. CXCR7 is reported to be expressed on endothelial cells in the synovium. Also, elevated levels of CXCL12 and CXCL11 mRNA were found in synovial tissue of rheumatoid arthritis patients (Ueno et al.; Rheumatol Int. 2005, 25(5):361-7). CXCL12 was shown to play a central role in CD4+ T cell and monocytes accumulation in the synovium (Nanki T et al.; J Immunol. 2000, 165(11):6590-8; Blades M C et al.; Arthritis Rheum. 2002 March; 46(3):824-36). In addition, CXCL12 participates in the rheumatoid arthritis process via its pro-angiogenic functions and its action on osteoclast recruitment and differentiation. Therefore, modulators of the CXCL12 pathway including CXCR7 modulators have been proposed as potential therapeutic agents to treat rheumatoid arthritis. Villalvilla et al (Expert Opin Ther Targets. 2014, 18(9): 1077-87) recently discussed preclinical and clinical data that support the potential use of anti-CXCL12 agents in rheumatoid arthritis treatments. Watanabe et al (Arthritis Rheum. 2010, 62(11):3211-20) teach that a CXCR7 inhibitor prophylactically and therapeutically reduces disease clinical signs and angiogenesis in a mouse collagen-induced arthritis model.

Specifically, CXCR7 is involved in several inflammatory disorders. For example, CXCL12 and CXCL11 are involved in acute and chronic lung inflammatory processes such as chronic obstructive pulmonary disease (Petty J M et al.; J Immunol. 2007, 178(12):8148-57; Porter J C et al.; J Immunol. 2008, 180(3):1866-77). CXCL12 was found upregulated in the lung in both humans and in animal models (Phillips R J et al.; J Clin Invest. 2004, 114(3):438-46). Knockdown of CXCR7 in the lung and anti-CXCL12 agents have been shown to attenuate lung inflammation and airway hyppereactivity in asthma models (Gasparik V et al.; ACS Med Chem Lett. 2012 Jan. 12; 3(1):10-4; Lukacs N W et al.; Am J Pathol. 2002, 160(4):1353-60). CXCR7 antagonism or CXCL12 blockade were shown to reduce pulmonary inflammation, stabilizating the pulmonary epithelial barrier in acute lung injury in mice (Ngamsri K C et al.; J Immunol. 2017, 198(6):2403-2413; Konrad F M et al.; Cell Death Dis. 2017, 8 (5)). Cao et al (Nat Med. 2016; 22(2):154-62) teach that CXCR7 modulator after lung injury "promotes alveolar repair and reduces fibrosis" in a mouse model of lung fibrosis. A role for CXCR7 in liver fibrosis was also described (Ding B S et al.; Nature. 2014, 505(7481):97-102).

CXCL12 and CXCL11 are also reported to be upregulated in Inflammatory bowel diseases (Koelink P J et al.; Pharmacol Ther. 2012, 133(1):1-18). CXCR7 was found upregulated on peripheral blood T cells in Inflammatory bowel diseases (Werner L et al.; J Leukoc Biol. 2011, 90(3):583-90). The author hypothetise that "the increased expression of CXCR7 in the peripheral blood of Inflammatory bowel diseases patients could foster increased influx of T cells to sites of mucosal inflammation" (Werner L et al.; Theranostics. 2013, 3(1):40-6). In mouse models for Inflammatory bowel disease, modulators of the CXCL12 pathway could decrease infiltration of T cells and reduce tissue damage (Mikami S et al.; J Pharmacol Exp Ther. 2008, 327(2):383-92; Xia X M et al.; PLoS One. 2011, 6(11):e27282).

Elevated levels of CXCL12 and CXCL11 have also been found in lesional psoriatic skin (Chen S C et al.; Arch Dermatol Res. 2010, 302(2):113-23; Zgraggen S et al.; PLoS One. 2014, 9(4):e93665). Zgraggen et al teach that blockade of CXCL12 improved the course of chronic skin inflammation in two different models of psoriasis-like skin inflammation.

Several other auto-immune disorders like systemic lupus erythematosus (SLE) display altered CXCR7/CXCR4 expression correlated with an impaired CXCL12-promoted migration of SLE B cells (Biajoux V et al.; J Transl Med. 2012, 18; 10:251). In addition, CXCL12 was significantly up-regulated in the nephritic kidneys in multiple murine models of lupus. Wang et al. (J Immunol. 2009, 182(7): 4448-58) teach that acting on the CXCL12 axis is a good therapeutic target in lupus, as a CXCR4 antagonist significantly ameliorates the disease, prolonging survival and reducing nephritis and lymphoproliferation.

CXCL12 and CXCR4 were found upregulated in thyroids from autoimmune patients and in animal models (Armengol M P et al.; J Immunol. 2003, 170(12):6320-8). Liu et al. (Mol Med Rep. 2016, 13(4):3604-12) teach that blocking of CXCR4 reduced the severity of autoimmune thyroiditis in mice, decreasing the lymphocytes infiltration and autoantibodies production.

Virani et al (Virani S et al.; AJRI. 2013, 70:386-397) teach that the blockade of CXCL12 limits angiogenesis in endometriosis lesions.

The biological properties of CXCR7 modulators also include, but are not limited to, any physiological function and/or cellular function linked and/or controlled by its ligands CXCL11, CXCL12, BAM22 and its related peptides. Hence, CXCL12 depletion sensitizes cancer cells to chemotherapy in vivo and CXCL12 treatment blocks colonic carcinoma metastasis (Duda et al.; Clin. Cancer Res. 2011 17(8) 2074-2080; Naumann et al.; Plos One. 2010, 5(2) e9175). CXCR7 is also a receptor for CXCL11 (alias small inducible cytokine subfamily b, member 11; scyb11, alias interferon-gamma-inducible protein 9; ip9, alias small inducible cytokine subfamily b, member 9b; scyb9b) and therefore modulators of CXCR7 activity can also be used in indications with CXCL11-associated pathology (Rupertus K et al.; Clin Exp Metastasis. 2014, 31(4):447-59; Zohar Y et al.; J Clin Invest. 2014, 124(5):2009-22; Antonelli A et al.; Thyroid. 2013, 23(11):1461-9). CXCR7 functions also as a receptor for the opioid peptide BAM22 and its related peptides (peptide E, peptides BAM12, BAM14, BAM18) and therefore modulators of CXCR7 activity possibly may also be used in indications with opioid peptides associated pathologies (Ikeda et al.; Cell. 2013, 155, 1323-1336). CXCR7 has also been shown to function as a scavenger receptor for CXCl11 and CXCL12. Thus, CXCR7 targeting has been shown to alter CXCl11 and CXCL12 local concentration leading to a deregulation of the CXCl11 and CXCL12 concentration gradients.

Certain isoxazole compounds which are SMYD protein blockers are known from WO2016/040515, wherein in the compounds of WO2016/040515, the isoxazole ring is substituted with certain (cyclo-)alkyl substituents instead of the present phenyl substituent; and the piperidine moiety does not carry a carboxamide substituent. Certain pyrrole compounds are known as antibacterial agents from WO2006/087543, WO2005/026149 and J. Med. Chem 2014, 57(14), 6060-6082. Cyclic diamines as Factor Xa inhibitors are known from WO2005/032490. WO2004/050024 discloses pyrrolidine compounds as chemokine receptor modulators.

The present invention provides novel crystalline forms of (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide which are modulators of the CXCR7 receptor, i.e. they act as CXCR7 receptor antagonists, and are useful for the prevention or treatment of diseases which respond to the activation of the CXCL12 receptors and/or CXCL11 receptors, especially cancer. In the prevention or treatment of cancers said crystalline forms may also be used in combination with one or more chemotherapy agents and/or radiotherapy and/or targeted therapy.

Figure 1:
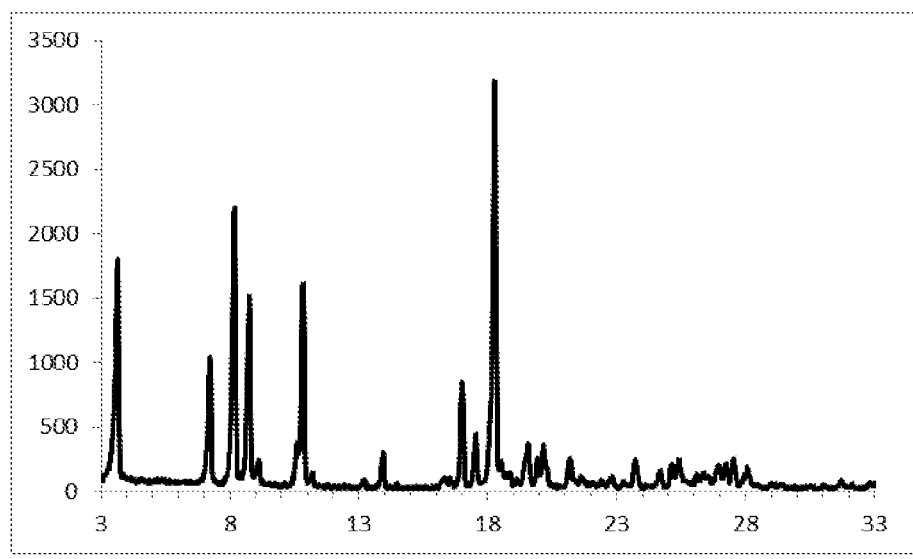
FIG. 1 shows the X-ray powder diffraction diagram of COMPOUND in a crystalline form 1 as obtained from Example 1. The X-ray diffraction measured with method 1 diagram shows peaks having a relative intensity, as compared to the most intense peak in the diagram, of the following percentages (relative peak intensitites given in parenthesis) at the indicated angles of refraction 2theta (selected peaks from the range 3-40° 2theta with significant intensity are reported): 3.6° (53%), 7.2° (31%), 8.2° (68%), 8.7° (46%), 9.1° (6%), 10.8° (50%), 13.9° (9%), 17.0° (26%), 17.5° (12%), 18.3° (100%).

For avoidance of any doubt, the above-listed peaks describe the experimental results of the X-ray powder diffraction shown in FIG. 1 to FIG. 4. It is understood that, in contrast to the above peak list, only a selection of characteristic peaks is required to fully and unambiguously characterize of the COMPOUND in the respective crystalline form of the present invention.

In the X-ray diffraction diagrams of FIG. 1 to FIG. 4 the angle of refraction 2theta (2θ) is plotted on the horizontal axis and the counts on the vertical axis.

DETAILED DESCRIPTION OF THE INVENTION

1) A first embodiment of the invention relates to crystalline forms of COMPOUND (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide

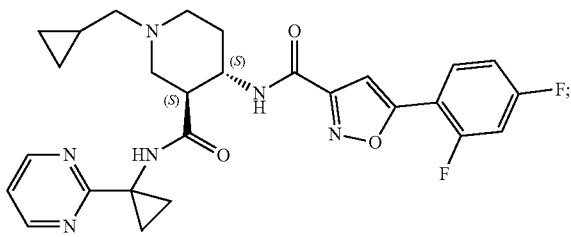

characterized by:
a. the presence of peaks in the X-ray powder diffraction diagram at the following angles of refraction 2θ: 3.6°, 8.2°, and 18.3° (notably 3.6°, 7.2°, 8.2°, 8.7°, and 18.3°; especially 3.6°, 7.2°, 8.2°, 8.7°, 9.1°, 10.8°, 13.9°, 17.0°, 17.5°, and 18.3°); or
b. the presence of peaks in the X-ray powder diffraction diagram at the following angles of refraction 2θ: 6.7°, 8.5°, and 10.9° (notably 6.7°, 8.5°, 10.9°, 13.2°, and 14.5°; especially 6.7°, 8.5°, 10.9°, 13.2°, 14.1°, 14.5°, 16.0°, 17.4°, 18.4°, and 20.8°); or
c. the presence of peaks in the X-ray powder diffraction diagram at the following angles of refraction 2θ: 8.2°, 17.9°, and 21.0° (notably 6.8°, 8.2°, 14.1°, 17.9°, and 21.0°; especially 6.8°, 8.2°, 8.8°, 14.1°, 16.0°, 17.9°, 21.0°, and 24.1°).

It is understood, that the crystalline forms according to embodiment 1) comprise COMPOUND (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide in a crystalline form of the free base (i.e. not in form of a salt). Furthermore, said crystalline forms may comprise non-coordinated and/or coordinated solvent. Coordinated solvent is used herein as term for a crystalline solvate. Likewise, non-coordinated solvent is used herein as term for physiosorbed or physically entrapped solvent (definitions according to Polymorphism in the Pharmaceutical Industry (Ed. R. Hilfiker, VCH, 2006), Chapter 8: U. J. Griesser: The Importance of Solvates). Crystalline form 1 in particular is an anhydrate, i.e. it comprises no coordinated water, but may comprise non-coordinated solvent such as isopropanol, methanol, ethanol and/or water. Crystalline form 2 in particular is an anhydrate, i.e. it comprises no coordinated water, but may comprise non-coordinated solvent such as isopropanol, methanol, ethanol and/or water. Cystalline form 3 in particular is a dihydrate, i.e. it comprises about 2 equivalents of coordinated water, and may comprise additional non-coordinated solvent such as water.

2) Another embodiment relates to a crystalline form of COMPOUND according to embodiment 1), characterized by the presence of peaks in the X-ray powder diffraction diagram at the following angles of refraction 2θ: 3.6°, 8.2°, and 18.3°; wherein said crystalline form is notably characterized by the presence of peaks in the X-ray powder diffraction diagram at the following angles of refraction 2θ: 3.6°, 7.2°, 8.2°, 8.7°, and 18.3°.

3) Another embodiment relates to a crystalline form of COMPOUND characterized by the presence of peaks in the X-ray powder diffraction diagram at the following angles of refraction 2θ: 3.6°, 8.2°, and 18.3° according to embodiment 1); or to such crystalline form according to embodiment 2), wherein said crystalline form is especially characterized by the presence of peaks in the X-ray powder diffraction diagram at the following angles of refraction 2θ: 3.6°, 7.2°, 8.2°, 8.7°, 9.1°, 10.8°, 13.9°, 17.0°, 17.5°, and 18.3°.

4) Another embodiment relates to a crystalline form of COMPOUND characterized by the presence of peaks in the X-ray powder diffraction diagram at the following angles of refraction 2θ: 3.6°, 8.2°, and 18.3° according to embodiment 1); or to such crystalline form according to embodiment 2) or 3), which essentially shows the X-ray powder diffraction pattern as depicted in FIG. 1.

5) Another embodiment relates to a crystalline form of COMPOUND characterized by the presence of peaks in the X-ray powder diffraction diagram at the following angles of refraction 2θ: 3.6°, 8.2°, and 18.3° according to embodiment 1); or to such crystalline form according to any one of embodiments 2) to 4), which has an endothermal event at about 259° C. as determined by differential scanning calorimetry (e.g. by using the method as described herein).

6) Another embodiment relates to a crystalline form of COMPOUND characterized by the presence of peaks in the X-ray powder diffraction diagram at the following angles of refraction 2θ: 3.6°, 8.2°, and 18.3° according to embodiment 1); or to such crystalline form according to any one of embodiments 2) to 5), wherein said form is obtainable by:
a) mixing 10 mg of COMPOUND with 1 mL of methanol, or mixing 20 mg of COMPOUND with 1 mL of an about 3 to 1 mixture of methanol and acetonitrile;
b) dissolving the COMPOUND by heating to about 65° C. with a ramp of 0.1° C./min;
c) cooling the mixture to about 20° C. by using a ramp of 0.1° C./min; and
d) filtering and drying the product (e.g. at room temperature and reduced pressure of about 10 mbar for 4 hours).

7) Another embodiment relates to a crystalline form of COMPOUND characterized by the presence of peaks in the X-ray powder diffraction diagram at the following angles of refraction 2θ: 3.6°, 8.2°, and 18.3° according to embodiment 1); or to such crystalline form according to any one of embodiments 2) to 6), wherein said crystalline form is an anhydrate (i.e. it contains no coordinated water).

8) Another embodiment relates to a crystalline form of COMPOUND according to embodiment 1, characterized by:
a. the presence of peaks in the X-ray powder diffraction diagram at the following angles of refraction 2θ: 6.7°, 8.5°, 10.9°, 13.2°, and 14.5°; or b. the presence of peaks in the X-ray powder diffraction diagram at the following angles of refraction 2θ: 6.8°, 8.2°, 14.1°, 17.9°, and 21.0°.

9) Another embodiment relates to a crystalline form of COMPOUND according to embodiments 1) or 8), characterized by:
   a. the presence of peaks in the X-ray powder diffraction diagram at the following angles of refraction 2θ: 6.7°, 8.5°, 10.9°, 13.2°, 14.1°, 14.5°, 16.0°, 17.4°, 18.4°, and 20.8°; or
   b. the presence of peaks in the X-ray powder diffraction diagram at the following angles of refraction 2θ: 6.8°, 8.2°, 8.8°, 14.1°, 16.0°, 17.9°, 21.0°, and 24.1°.

Figure 2:
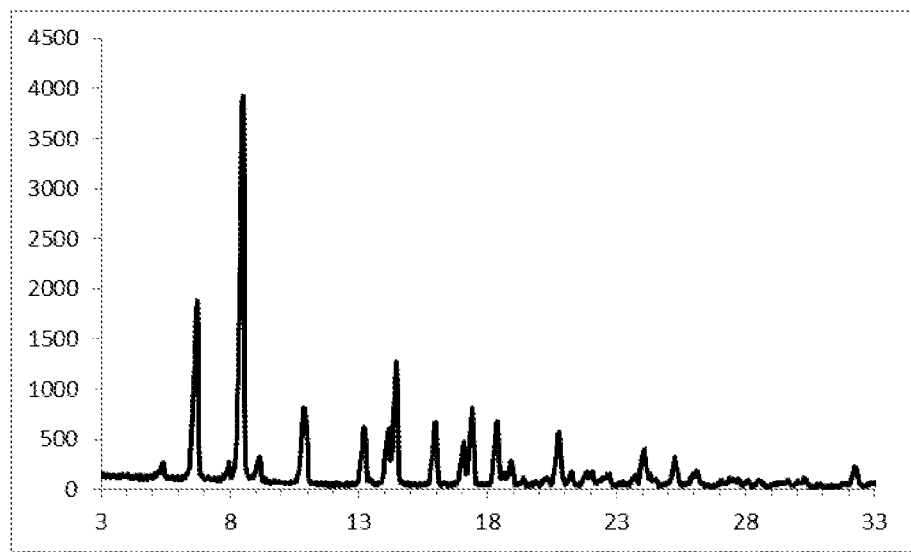
FIG. 2 shows the X-ray powder diffraction diagram of COMPOUND in a crystalline form 2 as obtained from Example 2. The X-ray diffraction diagram measured with method 1 shows peaks having a relative intensity, as compared to the most intense peak in the diagram, of the following percentages (relative peak intensitites given in parenthesis) at the indicated angles of refraction 2theta (selected peaks from the range 3-40° 2theta with significant intensity are reported): 6.7° (46%), 8.5° (100%), 10.9° (19%), 13.2° (15%), 14.1° (13%), 14.5° (31%), 16.0° (16%), 17.4° (20%), 18.4° (16%), 20.8° (14%).
Figure 3:
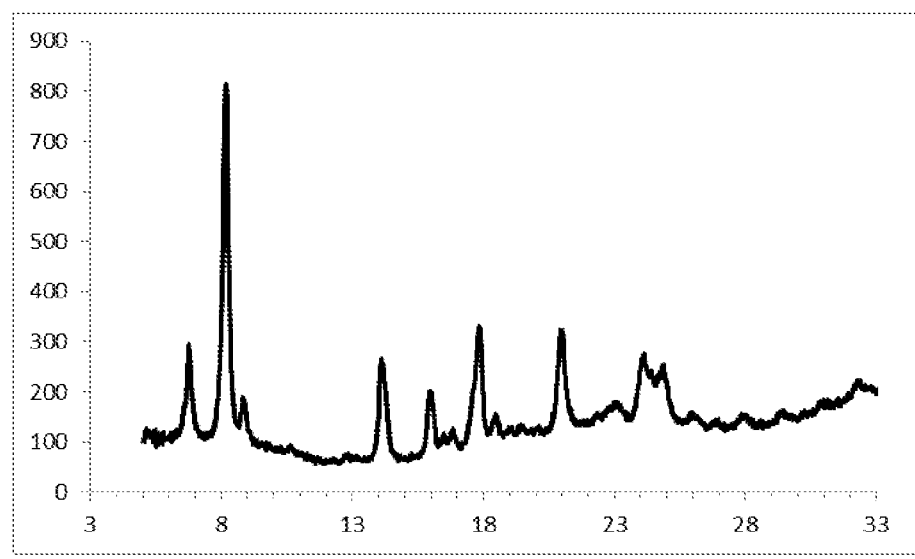
FIG. 3 shows the X-ray powder diffraction diagram of COMPOUND in a crystalline form 3 as obtained from Example 3. The X-ray diffraction diagram measured with method 2 shows peaks having a relative intensity, as compared to the most intense peak in the diagram, of the following percentages (relative peak intensitites given in parenthesis) at the indicated angles of refraction 2theta (selected peaks from the range 3-40° 2theta with significant intensity are reported): 6.8° (26%), 8.2° (100%), 8.8° (11%), 14.1° (27%), 16.0° (16%), 17.9° (31%), 21.0° (26%), 24.1° (17%).

10) Another embodiment relates to a crystalline form of COMPOUND according to embodiments 1) or 8), characterized by:
   a. the presence of peaks in the X-ray powder diffraction diagram at the following angles of refraction 2θ: 6.7°, 8.5°, 10.9° (notably 6.7°, 8.5°, 10.9°, 13.2°, and 14.5°); or to such crystalline form according to embodiment 9), which essentially shows the X-ray powder diffraction pattern as depicted in FIG. 2; or
   b. the presence of peaks in the X-ray powder diffraction diagram at the following angles of refraction 2θ: 8.2°, 17.9°, 21.0° (notably 6.8°, 8.2°, 14.1°, 17.9°, and 21.0°); or to such crystalline form according to embodiment 9), which essentially shows the X-ray powder diffraction pattern as depicted in FIG. 3.

11) Another embodiment relates to a crystalline form of COMPOUND according to embodiment 1, characterized by the presence of peaks in the X-ray powder diffraction diagram at the following angles of refraction 2θ: 6.7°, 8.5°, 10.9°, 13.2°, 14.5° (notably 6.7°, 8.5°, 10.9°, 13.2°, 14.1°, 14.5°, 16.0°, 17.4°, 18.4°, and 20.8°).

12) Another embodiment relates to a crystalline form of COMPOUND characterized by the presence of peaks in the X-ray powder diffraction diagram at the following angles of refraction 2θ: 6.7°, 8.5°, and 10.9° according to embodiment 1); or to such crystalline form according to any one of embodiments 8) to 11), wherein said crystalline form is an anhydrate (i.e. it contains no coordinated water).

13) Another embodiment relates to a crystalline form of COMPOUND according to embodiment 1, characterized by the presence of peaks in the X-ray powder diffraction diagram at the following angles of refraction 2θ: 6.8°, 8.2°, 14.1°, 17.9°, 21.0° (notably 6.8°, 8.2°, 8.8°, 14.1°, 16.0°, 17.9°, 21.0°, and 24.1°).

14) Another embodiment relates to a crystalline form of COMPOUND characterized by the presence of peaks in the X-ray powder diffraction diagram at the following angles of refraction 2θ: 8.2°, 17.9°, and 21.0° according to embodiment 1); or to such crystalline form according to any one of embodiments 8) to 10), or 13), wherein said crystalline form is a dihydrate (i.e. it contains about 2 equivalents of coordinated water; wherein it is understood that said about 2 equivalents of coordinated water correspond to a crystalline form of COMPOUND having a water content of about 6.9% (e.g. as determined by GVS/moisture sorption experiments).

Figure 4:
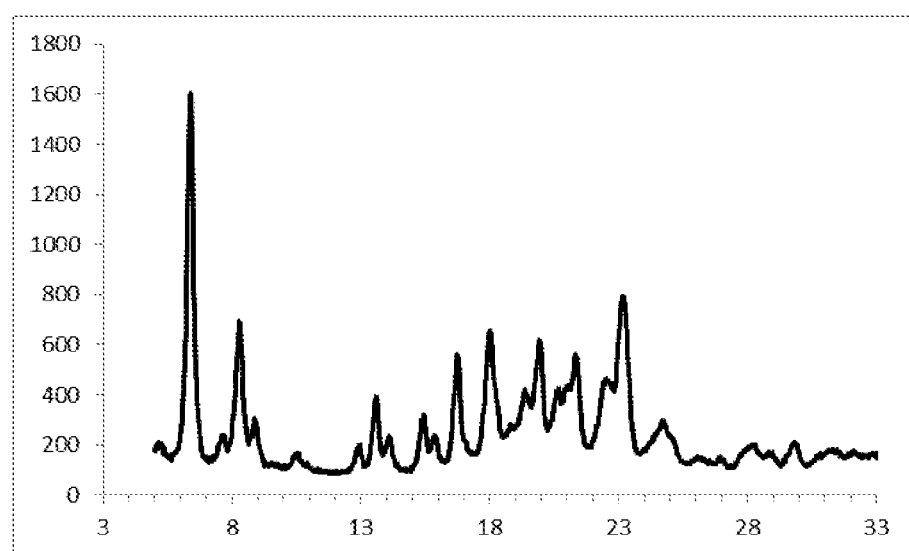
FIG. 4 shows the X-ray powder diffraction diagram of COMPOUND in a crystalline form 4 as obtained from Example 4. The X-ray diffraction diagram measured with method 2 shows peaks having a relative intensity, as compared to the most intense peak in the diagram, of the following percentages (relative peak intensitites given in parenthesis) at the indicated angles of refraction 2theta (selected peaks from the range 3-40° 2theta with significant intensity are reported): 6.4° (100%), 8.3° (38%), 8.9° (12%), 13.6° (20%), 14.1° (9%), 15.4° (14%), 16.7° (28%), 18.0° (32%), 23.2° (42%).

Further disclosed is (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide in crystalline form 4, which form is notably characterized by the presence of peaks in the X-ray powder diffraction diagram at the following angles of refraction 2θ: 6.4°, 8.3°, 16.7°, 18.0°, and 23.2° (especially 6.4°, 8.3°, 8.9°, 13.6°, 14.1°, 15.4°, 16.7°, 18.0°, and 23.2°); and which essentially shows the X-ray powder diffraction pattern as depicted in FIG. 4. Cystalline form 4 in particular may comprise additional coordinated or non-coordinated solvent such as THF and/or water.

For avoidance of any doubt, whenever one of the above embodiments refers to "peaks in the X-ray powder diffraction diagram at the following angles of refraction 2θ", said X-ray powder diffraction diagram is obtained by using combined Cu Kα1 and Kα2 radiation, without Kα2 stripping; and it should be understood that the accuracy of the 2θ values as provided herein is in the range of +/−0.1-0.2°. Notably, when specifying an angle of refraction 2theta (2θ) for a peak in the invention embodiments and the claims, the 2θ value given is to be understood as an interval from said value minus 0.2° to said value plus 0.2° (2θ+/−0.2°); and preferably from said value minus 0.1° to said value plus 0.1° (2θ+/−0.1°).

Where the plural form is used for compounds, solids, pharmaceutical compositions, diseases and the like, this is intended to mean also a single compound, solid, or the like.

The term "enantiomerically enriched" is understood in the context of the present invention to mean especially that at least 90, preferably at least 95, and most preferably at least 99 percent by weight of the COMPOUND are present in form of one enantiomer of the COMPOUND. It is understood that COMPOUND is present in enantiomerically enriched absolute (3S,4S)-configuration.

The term "essentially pure" is understood in the context of the present invention to mean especially that at least 90, preferably at least 95, and most preferably at least 99 percent by weight of the crystals of a COMPOUND are present in a crystalline form according to the present invention, especially in a single crystalline form of the present invention.

When defining the presence of peak in e.g. an X-ray powder diffraction diagram, a common approach is to do this in terms of the S/N ratio (S=signal, N=noise). According to this definition, when stating that a peak has to be present in an X-ray powder diffraction diagram, it is understood that the peak in the X-ray powder diffraction diagram is defined by having an S/N ratio (S=signal, N=noise) of greater than x (x being a numerical value greater than 1), usually greater than 2, especially greater than 3.

In the context with stating that the crystalline form essentially shows an X-ray powder diffraction pattern as depicted in FIG. 1 to FIG. 4, respectively, the term "essentially" means that at least the major peaks of the diagram depicted in said figures, i.e. those having a relative intensity of more than 10%, especially more than 20%, as compared to the most intense peak in the diagram, have to be present. However, the person skilled in the art of X-ray powder diffraction will recognize that relative intensities in X-ray powder diffraction diagrams may be subject to strong intensity variations due to preferred orientation effects.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., preferably to an interval extending from Y minus 5° C. to Y plus 5° C., notably to an interval extending from Y minus 3° C. to Y plus 3° C. Room temperature means a temperature of about 25° C. When in the current application the term n equivalent(s) is used wherein n is a number, it is meant and within the scope of the current application that n is referring to about the number n, preferably n is referring to the exact number n.

Whenever the word "between" or "to" is used to describe a numerical range, it is to be understood that the end points of the indicated range are explicitly included in the range. For example: if a temperature range is described to be between 40° C. and 80° C. (or 40° C. to 80° C.), this means that the end points 40° C. and 80° C. are included in the range; or if a variable is defined as being an integer between 1 and 4 (or 1 to 4), this means that the variable is the integer 1, 2, 3, or 4.

The expression % w/w refers to a percentage by weight compared to the total weight of the composition considered. Likewise, the expression v/v refers to a ratio by volume of the two components considered. The expression "vol" signifies volumes (in L, e.g. of solvent) per weight (in kg, e.g. of reactant). For example 7 vol signifies 7 liters (of solvent) per kg (of reactant).

The crystalline forms, especially the essentially pure crystalline forms, of COMPOUND according to any one of embodiments 1) to 14) can be used as medicaments, e.g. in the form of pharmaceutical compositions for enteral or parenteral administration.

15) Another embodiment thus relates to a crystalline form of COMPOUND (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to any one of embodiments 1) to 14) for use as a medicament.

The crystalline solid, especially the essentially pure crystalline solid, of COMPOUND according to any one of embodiments 1) to 14) may be used as single component or as mixtures with other crystalline forms or the amorphous form of COMPOUND.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the crystalline forms of the present invention, optionally in combination with other therapeutically valuable substances, into a galenical administration form together with suitable, non-toxic, inert, pharmaceutically acceptable solid or liquid carrier materials and, if desired, usual pharmaceutical adjuvants.

16) A further embodiment of the invention relates to pharmaceutical compositions comprising as active ingredient a crystalline form of COMPOUND (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to any one of embodiments 1) to 14), and at least one pharmaceutically acceptable carrier material.

Such pharmaceutical compositions according to embodiment 16) are especially useful for the prevention or treatment of prevention/prophylaxis or treatment of diseases or disorders relating to the CXCR7 receptor or its ligands.

17) A further embodiment of the invention relates to a pharmaceutical composition according to embodiment 14), wherein said pharmaceutical composition is in form of a tablet.

18) A further embodiment of the invention relates to a pharmaceutical composition according to embodiment 14), wherein said pharmaceutical composition is in form of a capsule.

19) A further embodiment of the invention relates to a crystalline form of COMPOUND (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to any one of embodiments 1) to 14) [especially the crystalline form according to any one of embodiments 2) to 7)], for use in the manufacture of a pharmaceutical composition, wherein said pharmaceutical composition comprises as active ingredient the COMPOUND (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide, and at least one pharmaceutically acceptable carrier material.

For avoidance of any doubt, embodiment 19) refers to the crystalline form according to any one of embodiments 1) to 14) [especially the crystalline form according to any one of embodiments 2) to 7)] which is suitable/which is used as final isolation step of COMPOUND (e.g. in order to meet the purity requirements of pharmaceutical production), whereas the final pharmaceutical composition according to embodiment 17) may or may not contain said crystalline form (e.g. because the originally crystalline form of COMPOUND is further transformed during the manufacturing process and/or is dissolved in the pharmaceutically acceptable carrier material(s); thus, in the final pharmaceutical composition, COMPOUND may be present in non-crystalline form, in another crystalline form, or in dissolved form, or the like).

20) A further embodiment of the invention thus relates to a pharmaceutical composition comprising as active ingredient the COMPOUND (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide, wherein said pharmaceutical composition is manufactured using a crystalline form of COMPOUND (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to any one of embodiments 1) to 14) [especially the crystalline form according to any one of embodiments 2) to 7)] and at least one pharmaceutically acceptable carrier material.

21) A further embodiment of the invention relates to a pharmaceutical composition according to embodiment 20), wherein said pharmaceutical composition is in form of a capsule.

22) A further embodiment of the invention relates to a crystalline form of COMPOUND (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to any one of embodiments 1) to 14), for use in the prevention/prophylaxis or treatment of diseases or disorders relating to the CXCR7 receptor or its ligands.

23) A further embodiment of the invention relates to a crystalline form of COMPOUND (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to any one of embodiments 1) to 14), for use in the preparation of a medicament for the prevention/prophylaxis or treatment of diseases or disorders relating to the CXCR7 receptor or its ligands.

The crystalline forms of COMPOUND as defined in any one of embodiments 1) to 14) are useful for the prevention/prophylaxis or treatment of diseases or disorders relating to the CXCR7 receptor or its ligands which are especially to disorders relating to a dysfunction of the CXCR7 receptor, or dysfunction of ligands signalling through CXCR7, or dysfunction of CXCR7 ligands (CXCL12 and CXCL11) signalling through their other receptors (CXCR4 and CXCR3).

Such diseases or disorders relating to the CXCR7 receptor or its ligands are especially selected from the group consisting of

- cancer (notably brain tumors including malignant gliomas, glioblastoma multiforme; neuroblastoma; pancreatic cancer including pancreatic adenocarcinoma/pancreatic ductal adenocarcinoma; gastro-intestinal cancers including colon carcinoma, hepatocellular carcinoma and gastric cancer; Kaposi's sarcoma; leukemias including adult T-cell leukemia; lymphoma; lung cancer; breast cancer; rhabdomyosarcoma; prostate cancer; esophageal squamous cancer; oral squamous cell carcinoma; endometrial cancer; thyroid carcinoma including papillary thyroid carcinoma; metastatic cancers; lung metastasis; skin cancer including melanoma and metastatic melanoma; bladder cancer; multiple myelomas; osteosarcoma; head and neck cancer; and renal carcinomas including renal clear cell carcinoma, metastatic renal clear cell carcinoma);
- inflammatory diseases (notably chronic rhinosinusitis, asthma, chronic obstructive pulmonary disorder, atherosclerosis, myocarditis, and sarcoidosis; especially chronic rhinosinusitis, asthma, and atherosclerosis);
- autoimmune disorders (notably (inflammatory) demyelinating diseases; multiple sclerosis (MS); Guillain Barré syndrome; rheumatoid arthritis (RA); inflammatory bowel diseases (IBD, especially comprising Crohn's disease and ulcerative colitis); systemic lupus erythematosus (SLE); lupus nephritis; interstitial cystitis; celiac disease; autoimmune encephalomyelitis; osteoarthritis; and type I diabetes; especially autoimmune disorders which have an inflammatory component such as (inflammatory) demyelinating diseases, multiple sclerosis, Guillain Barré syndrome, rheumatoid arthritis, inflammatory bowel diseases, systemic lupus erythematosus, lupus nephritis, and auto-immune encephalomyelitis);
- transplant rejection (notably renal allograft rejection, cardiac allograft rejection, and graft-versus-host diseases brought about by hematopoietic stem cell transplantation); and
- fibrosis (notably liver fibrosis, liver cirrhosis, lung fibrosis, especially idiopathic pulmonary fibrosis).

Notably such diseases or disorders relating to the CXCR7 receptor or its ligands are cancers, autoimmune disorders (especially autoimmune disorders which have an inflammatory component), and fibrosis.

In addition, further diseases or disorders relating to the CXCR7 receptor or its ligands are diseases involving CXCR7 and/or CXCL12 and/or CXCL11 mediated metastasis, chemotaxis, cell adhesion, trans-endothelial migration, cell proliferation and/or survival.

In addition, further particular diseases or disorders relating to the CXCR7 receptor or its ligands are proliferative diabetic retinopathy; West Nile virus encephalitis; pulmonary vascular diseases, acute renal failure, ischemia including cerebral ischemia, acute coronary syndrome, injured central nervous system, hyperlipidemia, hypertension, pulmonary hypertension, Shiga-toxin-associated heomolytic uremic syndrome, preeclampsia, vascular injury, HIV/AIDS, angiogenesis, and brain and neuronal dysfunctions (such as inflammatory components of Alzheimer's disease), stress-related disorders (such as anxiety, depression, and posttraumatic stress disorder), and diseases involving opioid receptors, endometriosis, autoimmune thyroiditis, choroidal neovascularization-associated diseases, aplastic anemia, Sjögren's disease and vitiligo. In a sub-embodiment, such a further particular disease or disorder relating to the CXCR7 receptor or its ligands is pulmonary hypertension.

The term "cancer" refers to all sorts of cancers such as carcinomas; adenocarcinomas; leukemias; sarcomas; lymphomas; myelomas; metastatic cancers; brain tumors; neuroblastomas; pancreatic cancers; gastro-intestinal cancers; lung cancers; breast cancers; prostate cancers; endometrial cancers; skin cancers; bladder cancers; head and neck cancers; neuroendocrine tumors; ovarian cancers; cervical cancers; oral tumors; nasopharyngeal tumors; thoracic cancers; and virally induced tumors.

Notably the term refers to brain tumors including brain metastases, malignant gliomas, glioblastoma multiforme, medulloblastoma, meningiomas; neuroblastoma; pancreatic cancer including pancreatic adenocarcinoma/pancreatic ductal adenocarcinoma; gastro-intestinal cancers including colon carcinoma, colorectal adenoma, colorectal adenocarcinoma, metastatic colorectal cancer, familial adenomatous polyposis (FAP), gastric cancer, gallbladder cancer, cholangiocarcinoma, hepatocellular carcinoma; Kaposi's sarcoma; leukemias including acute myeloid leukemia, adult T-cell leukemia; lymphomas including Burkitt's lymphoma, Hodgkin's lymphoma, MALT lymphoma, and primary intraocular B-Cell lymphoma; lung cancer including non-small cell lung cancer; breast cancer including triple negative breast carcinoma; rhabdomyosarcoma; prostate cancer including castrate-resistant prostate cancer; esophageal squamous cancer; (oral) squamous cell carcinoma; endometrial cancer; thyroid carcinoma including papillary thyroid carcinoma; metastatic cancers; lung metastasis; skin cancer including melanoma and metastatic melanoma; bladder cancer including urinary bladder cancer, urothelial cell carcinoma; multiple myelomas; osteosarcoma; head and neck cancer; and renal carcinomas including renal cell carcinoma renal clear cell carcinoma, metastatic renal cell carcinoma, metastatic renal clear cell carcinoma; as well as neuroendocrine tumors; ovarian cancer; cervical cancer; oral tumors; nasopharyngeal tumors; thoracic cancer; choriocarcinoma; Ewing's sarcoma; and virally induced tumors. Especially the term "cancer" refers to malignant glioma in particular glioblastoma multiforme, neuroblastoma; pancreatic cancers in particular pancreatic ductal adenocarcinoma; Kaposi's sarcoma; adult T-cell leukemia, lymphoma; lung cancer; breast cancer; rhabdomyosarcoma; prostate cancer; esophageal squamous cancer; (oral) squamous cell carcinoma; endometrial cancer; papillary thyroid carcinoma; metastatic cancer; lung metastasis; melanoma; bladder cancer; multiple myelomas; osteosarcoma; gastro-intestinal cancers, in particular colon carcinoma, hepatocellular carcinoma and gastric cancer; head and neck cancer; and renal clear cell carcinoma. Preferably the term "cancer" refers to malignant glioma, in particular glioblastoma multiforme; pancreatic cancers, in particular pancreatic ductal adenocarcinoma; papillary thyroid carcinoma; hepatocellular carcinoma; lung cancer; breast cancer; metastatic cancers; lung metastasis; melanoma; colon carcinoma; head and neck cancer; and renal clear cell carcinoma.

The crystalline forms of COMPOUND as defined in any one of embodiments 1) to 14) may in particular be useful as therapeutic agents for the prevention/prophylaxis or treatment of a cancer as defined before, which cancer is a metastatic cancer/a cancer which forms metastasis.

The crystalline forms of COMPOUND as defined in any one of embodiments 1) to 14) may in particular be useful as therapeutic agents for the prevention/prophylaxis or treatment of a cancer. They can be used as single therapeutic agents or in combination with one or more chemotherapy agents and/or radiotherapy and/or targeted therapy. In a sub-embodiment, when a compound of formula (I) is used for the prevention/prophylaxis or treatment of a cancer in combination with one or more chemotherapy agents and/or radiotherapy and/or targeted therapy, such cancer is especially a malignant glioma, in particular a glioblastoma multiforme; pancreatic cancer, especially pancreatic ductal adenocarcinoma; papillary thyroid carcinoma; lung metastasis; melanoma; lung cancer; metastatic cancers; hepatocellular carcinoma; breast cancer; colorectal cancer; or head and neck cancer. Such combined treatment may be effected simultaneously, separately, or over a period of time.

The invention, thus, also relates to pharmaceutical compositions comprising a pharmaceutically acceptable carrier material, and:
- a crystalline form of COMPOUND as defined in any one of embodiments 1) to 14);
- and one or more cytotoxic chemotherapy agents.

The invention, thus, further relates to a kit comprising
- a pharmaceutical composition, said composition comprising a pharmaceutically acceptable carrier material, and a crystalline forms of COMPOUND as defined in any one of embodiments 1) to 14);
- and instructions how to use said pharmaceutical composition for the prevention or the treatment of a cancer (especially of a malignant glioma, in particular of a glioblastoma multiforme), in combination with chemotherapy and/or radiotherapy and/or targeted therapy.

The terms "radiotherapy" or "radiation therapy" or "radiation oncology", refer to the medical use of ionizing radiation in the prevention (adjuvant therapy) and/or treatment of cancer; including external and internal radiotherapy.

The term "targeted therapy" refers to the prevention/prophylaxis (adjuvant therapy) and/or treatment of cancer with one or more anti-neoplastic agents such as small molecules or antibodies which act on specific types of cancer cells or stromal cells. Some targeted therapies block the action of certain enzymes, proteins, or other molecules involved in the growth and spread of cancer cells. Other types of targeted therapies help the immune system kill cancer cells (immunotherapies); or deliver toxic substances directly to cancer cells and kill them. An example of a targeted therapy which is in particular suitable to be combined with the compounds of the present invention is immunotherapy, especially immunotherapy targeting the programmed cell death receptor 1 (PD-1 receptor) or its ligand PD-L1 (Feig C et al, PNAS 2013).

When used in combination with the compounds of formula (I), the term "targeted therapy" especially refers to agents such as:
a) Epidermal growth factor receptor (EGFR) inhibitors or blocking antibodies (for example Gefitinib, Erlotinib, Afatinib, Icotinib, Lapatinib, Panitumumab, Zalutumumab, Nimotuzumab, Matuzumab and Cetuximab);
b) B-RAF inhibitors (for example Vemurafenib, Sorafenib, Dabrafenib, GDC-0879, PLX-4720, LGX818);
c) Aromatase inhibitors (for example Exemestane, Letrozole, Anastrozole, Vorozole, Formestane, Fadrozole);
d) Immune Checkpoint inhibitors (for example, anti-PD1 antibodies such as Pembrolizumab (Lambrolizumab, MK-3475), Nivolumab, Pidilizumab, AMP-514/MED10680; small molecule anti PD1 agents such as for example compounds disclosed in WO2015/033299, WO2015/044900 and WO2015/034820; anti-PD1L antibodies, such as BMS-936559, atezolizumab (MPDL3280A), MEDI4736, avelumab (MSB0010718C); anti-PDL2, such as AMP224, anti-CTLA-4 antibodies, such as ipilimumab, tremilmumab);
e) Vaccination approaches (for example dendritic cell vaccination, peptide or protein vaccination (for example with gp100 peptide or MAGE-A3 peptide);
f) Re-introduction of patient derived or allogenic (non-self) cancer cells genetically modified to secrete immunomodulatory factors such as granulocyte monocyte colony stimulating factor (GMCSF) gene-transfected tumor cell vaccine (GVAX) or Fms-related tyrosine kinase 3 (Flt-3) ligand gene-transfected tumor cell vaccine (FVAX), or Toll like receptor enhanced GM-CSF tumor based vaccine (TEGVAX);
g) T-cell based adoptive immunotherapies, including chimeric antigen receptor (CAR) engineered T-cells (for example CTL019);
h) Cytokine or immunocytokine based therapy (for example Interferon alpha, interferon beta, interferon gamma, interleukin 2, interleukin 15);
i) Toll-like receptor (TLR) agonists (for example resiquimod, imiquimod, glucopyranosyl lipid A, CpG oligodesoxynucleotides);
j) Thalidomide analogues (for example Lenalidomide, Pomalidomide);
k) Indoleamin-2,3-Dioxgenase (IDO) and/or Tryptophane-2,3-Dioxygenase (TDO) inhibitors (for example NLG919/Indoximod, 1MT (1-methyltryptophan), INCB024360);
l) Activators of T-cell co-stimulatory receptors (for example anti-Lymphocyte-activation gene 3 (LAG-3) antibodies (such as BMS-986016); anti T cell immunoglobulin mucin-3 (TIM-3) antibodies, anti-CD137/4-1BB antibodies (for example BMS-663513/urelumab), anti-Killer-cell immunoglobulin-like receptors (KIR) for example Lirilumab (IPH2102/BMS-986015); anti-OX40/CD134 (Tumor necrosis factor receptor superfamily, member 4), anti OX40-Ligand/CD252; anti-glucocorticoid-induced TNFR family related gene (GITR) (such as TRX518), anti-CD40 (TNF receptor superfamily member 5) antibodies (such as CP-870,893); anti-CD40-Ligand antibodies (such as BG9588); anti-CD28 antibodies);
m) Molecules binding a tumor specific antigen as well as a T-cell surface marker such as bispecific antibodies or antibody fragments, antibody mimetic proteins such as designed ankyrin repeat proteins (DARPINS), bispecific T-cell engager (BITE, for example AMG103, AMG330);
n) Antibodies or small molecular weight inhibitors targeting colony-stimulating factor-1 receptor (CSF-1R) (for example RG7155 or PLX3397).

When used in combination with the crystalline forms of COMPOUND as defined in any one of embodiments 1) to 14), immune checkpoint inhibitors such as those listed under d), and especially those targeting the programmed cell death receptor 1 (PD-1 receptor) or its ligand PD-L1, are preferred.

The term "chemotherapy" refers to the treatment of cancer with one or more cytotoxic anti-neoplastic agents ("cytotoxic chemotherapy agents"). Chemotherapy is often used in conjunction with other cancer treatments, such as radiation therapy or surgery. The term especially refers to conventional chemotherapeutic agents which act by killing cells that divide rapidly, one of the main properties of most cancer cells. Chemotherapy may use one drug at a time (single-agent chemotherapy) or several drugs at once (combination chemotherapy or polychemotherapy). Chemotherapy using drugs that convert to cytotoxic activity only upon light exposure is called photochemotherapy or photodynamic therapy.

The term "cytotoxic chemotherapy agent" or "chemotherapy agent" as used herein refers to an active antineoplastic agent inducing apoptosis or necrotic cell death. When used in combination with the compounds of formula (I), the term especially refers to conventional cytotoxic chemotherapy agents such as:

a) alkylating agents (for example mechlorethamine, chlorambucil, cyclophosphamide, ifosfamide, streptozocin, carmustine, lomustine, melphalan, busulfan, dacarbazine, temozolomide, thiotepa or altretamine; in particular temozolomide);

b) platinum drugs (for example cisplatin, carboplatin or oxaliplatin);

c) antimetabolite drugs (for example 5-fluorouracil, capecitabine, 6-mercaptopurine, methotrexate, gemcitabine, cytarabine, fludarabine or pemetrexed);

d) anti-tumor antibiotics (for example daunorubicin, doxorubicin, epirubicin, idarubicin, actinomycin-D, bleomycin, mitomycin-C or mitoxantrone);

e) mitotic inhibitors (for example paclitaxel, docetaxel, ixabepilone, vinblastine, vincristine, vinorelbine, vindesine or estramustine); or f) topoisomerase inhibitors (for example etoposide, teniposide, topotecan, irinotecan, diflomotecan or elomotecan).

When used in combination with the crystalline forms of COMPOUND as defined in any one of embodiments 1) to 14), preferred cytotoxic chemotherapy agents are the abovementioned alkylating agents (notably mechlorethamine, chlorambucil, cyclophosphamide, ifosfamide, streptozocin, carmustine, lomustine, melphalan, busulfan, dacarbazine, 3-methyl-(triazen-1-yl)imidazole-4-carboxamide (MTIC) and prodrugs thereof such as especially temozolomide, thiotepa, altretamine; or pharmaceutically acceptable salts of these compounds; in particular temozolomide); and mitotic inhibitors (notably paclitaxel, docetaxel, ixabepilone, vinblastine, vincristine, vinorelbine, vindesine, estramustine; or pharmaceutically acceptable salts of these compounds; in particular paclitaxel). Most preferred cytotoxic chemotherapy agents to be used in combination with the compounds of formula (I) are those routinely used in the treatment of glioblastoma multiforme, in particular temozolomide. Equally preferred is radiotherapy.

Chemotherapy may be given with a curative intent or it may aim to prolong life or to palliate symptoms.

a) Combined modality chemotherapy is the use of drugs with other cancer treatments, such as radiation therapy or surgery.

b) Induction chemotherapy is the first line treatment of cancer with a chemotherapeutic drug. This type of chemotherapy is used for curative intent.

c) Consolidation chemotherapy is the given after remission in order to prolong the overall disease free time and improve overall survival. The drug that is administered is the same as the drug that achieved remission.

d) Intensification chemotherapy is identical to consolidation chemotherapy but a different drug than the induction chemotherapy is used.

e) Combination chemotherapy involves treating a patient with a number of different drugs simultaneously. The drugs differ in their mechanism and side effects. The biggest advantage is minimising the chances of resistance developing to any one agent. Also, the drugs can often be used at lower doses, reducing toxicity.

f) Neoadjuvant chemotherapy is given prior to a local treatment such as surgery, and is designed to shrink the primary tumor. It is also given to cancers with a high risk of micrometastatic disease.

g) Adjuvant chemotherapy is given after a local treatment (radiotherapy or surgery). It can be used when there is little evidence of cancer present, but there is risk of recurrence. It is also useful in killing any cancerous cells that have spread to other parts of the body. These micrometastases can be treated with adjuvant chemotherapy and can reduce relapse rates caused by these disseminated cells.

h) Maintenance chemotherapy is a repeated low-dose treatment to prolong remission.

i) Salvage chemotherapy or palliative chemotherapy is given without curative intent, but simply to decrease tumor load and increase life expectancy. For these regimens, a better toxicity profile is generally expected.

When combined with the crystalline forms of COMPOUND as defined in any one of embodiments 1) to 14), preventive or curative forms of chemotherapy (or mutatis mutandis: radiotherapy) such as those listed under a), b) c), d), e), and especially g) and/or h) above are preferred.

"Simultaneously", when referring to an administration type, means in the present application that the administration type concerned consists in the administration of two or more active ingredients and/or treatments at approximately the same time; wherein it is understood that a simultaneous administration will lead to exposure of the subject to the two or more active ingredients and/or treatments at the same time. When administered simultaneously, said two or more active ingredients may be administered in a fixed dose combination, or in an equivalent non-fixed dose combination (e.g. by using two or more different pharmaceutical compositions to be administered by the same route of administration at approximately the same time), or by a non-fixed dose combination using two or more different routes of administration; wherein said administration leads to essentially simultaneous exposure of the subject to the two or more active ingredients and/or treatments.

"Fixed dose combination", when referring to an administration type, means in the present application that the administration type concerned consists in the administration of one single pharmaceutical composition comprising the two or more active ingredients.

"Separately", when referring to an administration type, means in the present application that the administration type concerned consists in the administration of two or more active ingredients and/or treatments at different points in time; wherein it is understood that a separate administration will lead to a treatment phase (e.g. at least 1 hour, notably at least 6 hours, especially at least 12 hours) where the subject is exposed to the two or more active ingredients and/or treatments at the same time; wherein such "separate administration" may under certain circumstances also encompass a treatment phase where for a certain period of time (e.g. at least 12 hours, especially at least one day) the subject is exposed to only one of the two or more active ingredients and/or treatments. Separate administration thus especially refers to situations wherein one active ingredient and/or treatment is given e.g. once a day, and another is given e.g. twice a day, thrice a day, every other day, wherein as a consequence of such administration type the subject is exposed to the two or more active ingredients and/or treatments the same time during essentially the whole treatment period. Separate administration also refers to situations wherein at least one of the active ingredients and/or treatments is given with a periodicity substantially longer than daily (such as once or twice daily) administration (e.g. wherein one active ingredient and/or treatment is given e.g. once or twice a day, and another is given once a week). For example when used in combination with (e.g. weekly or bi-weekly) radiotherapy the present crystalline forms of COMPOUND as defined in any one of embodiments 1) to 14) would possibly be used "separately".

By administration "over a period of time" is meant in the present application the subsequent administration of two or more active ingredients and/or treatments at different times. The term in particular refers to an administration method according to which the entire administration of one of the active ingredients and/or treatments is completed before the administration of the other/the others begins. In this way it is possible to administer one of the active ingredients and/or treatments for several months before administering the other active ingredient(s) and/or treatment(s).

Administration "over a period of time" also encompasses situations wherein the crystalline forms of COMPOUND as defined in any one of embodiments 1) to 14) would be used in a treatment that starts after termination of an initial chemotherapeutic or radiotherapeutic treatment or targeted therapy (for example an induction chemotherapy), wherein optionally said treatment would be in combination with a further/an ongoing chemotherapeutic or radiotherapeutic treatment or targeted therapy treatment (for example in combination with a consolidation chemotherapy, an intensification chemotherapy, an adjuvant chemotherapy, or a maintenance chemotherapy; or radiotherapeutic equivalents thereof); wherein such further/ongoing chemotherapeutic or radiotherapeutic treatment or targeted therapy would be simultaneously or separately with the treatment using the crystalline forms of COMPOUND as defined in any one of embodiments 1) to 14).

Autoimmune disorders may be defined as comprising (inflammatory) demyelinating diseases; multiple sclerosis (MS); Guillain Barré syndrome; rheumatoid arthritis (RA); inflammatory bowel disease (IBD, especially comprising Crohn's disease and ulcerative colitis); systemic lupus erythematosus (SLE); lupus nephritis; interstitial cystitis; celiac disease; autoimmune encephalomyelitis; osteoarthritis; and type I diabetes. In addition, autoimmune diseases further comprise disorders such as psoriasis; psoriatic arthritis; antiphospholipid syndrome; thyroiditis such as Hashimoto's thyroiditis; lymphocytic thyroiditis; myasthenia gravis; uveitis; episcleritis; scleritis; Kawasaki's disease; uveoretinitis; posterior uveitis; uveitis associated with Behcet's disease; uveomeningitis syndrome; allergic encephalomyelitis; atopic diseases such as rhinitis, conjunctivitis, dermatitis; and post-infectious autoimmune diseases including rheumatic fever and post-infectious glomerulonephritis. In a sub-embodiment, autoimmune disorders especially refer to autoimmune disorders which have an inflammatory component wherein particular examples are (inflammatory) demyelinating diseases, multiple sclerosis (MS), Guillain Barré syndrome, rheumatoid arthritis (RA), inflammatory bowel disease (IBD, especially comprising Crohn's disease and ulcerative colitis), systemic lupus erythematosus (SLE), lupus nephritis, and auto-immune encephalomyelitis.

Inflammatory diseases may be defined as comprising especially chronic rhinusitis, as well as asthma, chronic obstructive pulmonary disorder (COPD), atherosclerosis, myocarditis, dry eye disease, sarcoidosis, inflammatory myopathies, and acute lung injury.

Transplant rejection may be defined as comprising rejection of transplanted organs such as kidney, liver, heart, lung, pancreas, cornea, and skin; graft-versus-host diseases brought about by hematopoietic stem cell transplantation; chronic allograft rejection and chronic allograft vasculopathy.

Fibrosis may be defined as comprising especially liver fibrosis, liver cirrhosis, lung fibrosis, idiopathic pulmonary fibrosis, renal fibrosis, endomyocardial fibrosis, and arthrofibrosis.

The crystalline forms of COMPOUND as defined in any one of embodiments 1) to 14) are also useful in method of prophylaxis or treating tumors comprising administering an effective amount of said crystalline form wherein said effective amount leads to a change of tumor properties, and wherein said modification is achieved by modulating the CXCL11/CXCL12 receptor pathway; wherein said prophylaxis or treatment may optionally be effected in combination with a conventional chemotherapeutic or radiotherapeutic treatment (in which case the tumor is notably a malignant glioma, in particular a glioblastoma multiforme). Such combined treatment may be effected simultaneously, separately, and/or over a period of time.

The crystalline forms of COMPOUND as defined in any one of embodiments 1) to 14) are also useful in method of modulating an immune response comprising the administration of an effective amount of said crystalline form wherein said effective amount modulates an inflammatory disease and wherein said response is mediated by the CXCL11/CXCL12 receptor pathway.

The present invention also relates to a process for the preparation of COMPOUND in enantiomerically enriched form, and to processes for the preparation and characterization of the crystalline forms of COMPOUND according to any one of embodiments 1) to 14). Said processes are described in the procedures of the experimental part below.

Experimental Procedures:

All temperatures are stated in ° C. Commercially available starting materials are used as received without further purification. Unless otherwise specified, all reactions are carried out in oven-dried glassware under an atmosphere of nitrogen or argon. Compounds are purified by flash column chromatography on silica gel or by preparative HPLC. Compounds described in the invention are characterised by LC-MS data (retention time $t_R$ is given in min; molecular weight obtained from the mass spectrum is given in g/mol) using the conditions listed below. In cases where compounds of the present invention appear as a mixture of conformational isomers, particularly visible in their LC-MS spectra, the retention time of the most abundant conformer is given.

NMR Spectroscopy

Bruker Avance II spectrometer equipped with a 400 MHz ($^1$H) Ultrashield™ Magnet and a BBO 5 mm probehead or a PAXTI 1 mm probehead, or a Bruker Avance III HD Ascend 500 MHz ($^1$H), magnet equipped with DCH cryoprobe. Chemical shifts (δ) are reported in parts per million (ppm) relative to proton resonances resulting from incomplete deuteration of the NMR solvent, e.g. for dimethylsulfoxide δ(H) 2.49 ppm, for chloroform δ(H) 7.24 ppm. The abbreviations s, d, t, q and m refer to singlet, doublet, triplet, quartet, multiplet and br to broad, respectively. Coupling constants J are reported in Hz.

Quality Control (QC) Analytical LC-MS:
Equipment and Conditions:
Pump: Waters Acquity Binary, Solvent Manager, MS: Waters SQ Detector, DAD: Acquity UPLC PDA Detector, ELSD: Acquity UPLC ELSD. Columns: Acquity UPLC CSH C18 1.7 µm 2.1×50 mm or Acquity UPLC HSS T3 C18 1.8 µm 2.1×50 mm from Waters, thermostated in the Acquity UPLC Column Manager at 60° C. Eluents: A1: H2O+0.05% FA; B1: AcCN+0.045% FA. Method: Gradient: 2% B 98% B over 2.0 min. Flow: 1.0 mL/min. Detection: UV 214 nm and ELSD, and MS, tR is given in min.

Analytical LC-MS

Equipment:

Binary gradient pump Agilent G4220A or equivalent with mass spectrometry detection (single quadrupole mass analyser, Thermo Finnigan MSQPlus or equivalent).

Conditions:

Method A (acidic conditions): Column: Zorbax SB-aq (3.5 µm, 4.6×50 mm); conditions: MeCN [eluent A]; water+0.04% TFA [eluent B]; gradient: 95% B→5% B over 1.5 min (flow: 4.5 mL/min). Detection: UV/Vis+MS.

Preparative LC-MS

Equipment:

Binary gradient pump Gilson 333/334 or equivalent with mass spectrometry detection (single quadrupole mass analyser, Thermo Finnigan MSQPlus or equivalent).

Conditions:

Method B (basic conditions): Column: Waters XBridge C18 (10 µm, 30×75 mm); conditions: MeCN [eluent A]; water+0.5% NH$_4$OH (25% aq.) [eluent B]; gradient: 95% B→5% B, over 6.5 min (flow: 75 mL/min). Detection: UV/Vis+MS.

Chiral Analytical Chromatography

Equipment:

HPLC: Dionex HPG-3200SD pump with a Dionex DAD-3000 UV detector.

SFC: CO$_2$ supply: Aurora Fusion A5 Evolution; pump: Agilent G4302A; UV detector: Agilent G1315C.

Conditions:

HPLC: Columns: ChiralPak AY-H, 5 µm, 250×4.6 mm or Regis (R,R) Whelk-O1 250×4.6 mm, 5 µm; eluent: A: Hept, 0.05% DEA, B: Ethanol, 0.05% DEA, flow 0.8 to 1.2 mL/min.

SFC Column: Regis (R,R) Whelk-O1, 4.6×250 mm, 5 µM; eluent: A: 60% CO$_2$, B: 40% DCM/EtOH/DEA 50:50:0.1

Chiral Preparative Chromatography

Equipment:

HPLC: 2 Varian SD1 pump with a Dionex DAD-3000 UV detector.

SFC: CO$_2$ supply: Maximator DLE15-GG-C; pumps: 2 SSI HF CP 300; UV detector: Dionex DAD-3000.

Conditions:

HPLC: Columns: ChiralPak IA, IB, IC, IE, or IF, 5 µm, 20×250 mm, or Regis (R,R) Whelk-O1, 21.1×250 mm, 5 µm; eluent: appropriate mixture of A (0% to 90% Hept) and B (10% to 100% EtOH, 0.1% DEA), flow: appropriate flow of 16, 23 or 34 mL/min.

SFC: Columns: Regis (R,R) Whelk-O1, 30×250 mm, 5 µm or ChiralPak IC, 30×250 mm, 5 µm; eluent: appropriate mixture of A (60% to 80% CO$_2$), and B (30% to 40% of DCM/EtOH/DEA 50:50:0.1), flow 160 mL/min.

X-Ray Powder Diffraction Analysis (XRPD)

XRPD Method 1:

X-ray powder diffraction patterns are collected on a Bruker D8 Advance X-ray diffractometer equipped with a Lynxeye detector operated with CuKα-radiation in reflection mode (coupled two Theta/Theta). Typically, the X-ray tube is run at of 40 kV/40 mA. A step size of 0.02° (2θ) and a step time of 76.8 sec over a scanning range of 3-50° in 2θ are applied. The divergence slit is set to fixed 0.3. Powders are slightly pressed into a silicon single crystal sample holder with depth of 0.5 mm and samples are rotated in their own plane during the measurement. Diffraction data are reported using combined Cu Kα1 and Kα2 radiation, without Kα2 stripping. The accuracy of the 2θ values as provided herein is in the range of +/−0.1-0.2° as it is generally the case for conventionally recorded X-ray powder diffraction patterns.

XRPD Method 2:

X-ray powder diffraction patterns are collected on a Bruker D8 GADDS-HTS diffractometer equipped with an automated XYZ stage, laser video microscope for auto-sample positioning and a Vantec-500 detector operated with CuKα-radiation in reflection mode. Typically, the X-ray tube is run at 40 kV/40 mA. X-ray optics consists of a single Göbel multilayer mirror coupled with a pinhole collimator of 0.5 mm. Typically a single frame is recorded over 180 s with goniometer positions of theta1 at 4° and theta2 at 16° and detector distance of 20 cm. The frame is integrated in the range of 5-35° 2θ. Samples run under ambient conditions are prepared as flat plate specimens using powder as received without grinding. Approximately 5-10 mg of sample is lightly pressed on a glass slide to obtain a flat surface. The sample is not moved over the measurement time. Diffraction data are reported using combined Cu Kα1 and Kα2 radiation, without Kα2 stripping. The accuracy of the 2θ values as provided herein is in the range of +/−0.1-0.2° as it is generally the case for conventionally recorded X-ray powder diffraction patterns.

Gravimetric Vapour Sorption (GVS) Analysis

Measurements are performed on a multi sample instrument SPS-100n (Projekt Messtechnik, Ulm, Germany) operated in stepping mode at 25° C. The sample is allowed to equilibrate at 40% RH before starting a pre-defined humidity program (40-0-95-0-95-40% RH, steps of 5% ΔRH and with a maximal equilibration time of 24 hours per step are applied. About 20 to 30 mg of each sample is used. The hygroscopic classification is done according to the European Pharmacopeia Technical Guide (1999, page 86), e.g., slightly hygroscopic: increase in mass is less than 2% and equal to or greater than 0.2% mass/mass; hygroscopic: increase in mass is less than 15% and equal to or greater than 2% mass/mass. The mass change between 40% relative humidity and 80% relative humidity in the first adsorption scan is considered.

Differential Scanning Calorimetry (DSC)

DSC data are collected on a Mettler Toledo STARe System (DSC822e module, measuring cell with ceramic sensor and STAR software version 9.20) equipped with a 34 position auto-sampler. The instrument is calibrated for energy and temperature using certified indium. Typically 1-5 mg of each sample, in an automatically pierced aluminium pan, is heated at 10° C. min$^{-1}$, unless stated otherwise, from −20° C. to 280° C. A nitrogen purge at 20 mL min$^{-1}$ is maintained over the sample. Peak temperatures are reported for melting points.

Thermogravimetric Analysis (TGA)

TGA data are collected on a Mettler Toledo STARe System (TGA851e module and STAR software version 9.20) equipped with a 34 position auto-sampler. Typically about 5 mg of a sample, in an automatically pierced aluminium pan, is heated at 10° C. min$^{-1}$, unless stated otherwise, from 30° C. to 250° C. A nitrogen purge at 10 mL min$^{-1}$ is maintained over the sample.

| Abbreviations (as used hereinbefore or hereinafter): | |
|---|---|
| aq. | aqueous |
| Boc | butyloxycarbonyl |
| d | days |
| DCM | dichloromethane |
| DEA | diethylamine |
| DIPEA | diisopropyl-ethylamine, Hünig's base, ethyl-diisopropylamine |
| DMF | dimethylformamide |
| DMSO | dimethylsulfoxide |
| Et | ethyl |
| EtOAc | ethyl acetate |
| EtOH | ethanol |
| FC | flash chromatography |
| h | hour(s) |
| HATU | 2-(7-Aza-1H-benzotriazole-1-yl)-1,1,3,3-tetramethyluronium hexafluorophosphate |
| Hept | heptane |
| HPLC | high performance liquid chromatography |
| HV | high vacuum conditions |
| LC-MS | liquid chromatography - mass spectrometry |
| Me | methyl |
| MeCN | acetonitrile |
| MeOH | methanol |
| mL | milliliter |
| min | minute(s) |
| Nr | number |
| Ph | phenyl |
| prep. | Preparative |
| rpm | rounds per minute |
| RT | room temperature |
| s | second(s) |
| sat. | Saturated |
| SFC | supercritical fluid chromatography |
| tBu | tert-butyl = tertiary butyl |
| TEA | triethylamine |
| TFA | trifluoroacetic acid |
| THF | tetrahydrofuran |
| $T_3P$ | Propylphosphonic anhydride |
| $t_R$ | retention time |

Reference Example 1

(3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide 4-((S)-1-Phenyl-ethylamino)-5,6-dihydro-2H-pyridine-1,3-dicarboxylic acid 1-tert-butyl ester 3-ethyl ester In a dry flask equipped with a Dean-Stark trap and reflux condenser, 4-oxopiperidine-1,3-dicarboxylic acid-1-t-butyl ester 3-ethyl ester (10 g, 37 mmol) is dissolved in toluene (150 mL). (S)-(−)-α-methylbenzylamine (6.71 g, 55.4 mmol) and p-toluenesulfonic acid monohydrate (0.36 g, 1.85 mmol) are added and the mixture is heated to reflux for 3 h. The mixture is then cooled to RT, washed three times with aq. sat. $NaHCO_3$ (3×100 mL) and dried over $MgSO_4$, filtered and concentrated under reduced pressure to yield the product as a thick yellow oil. LC-MS method A: $t_R$=1.01 min; $[M+H]^+$=375.18. $^1H$ NMR (400 MHz, $CDCl_3$) δ: 9.28 (d, J=7.4 Hz, 1H), 7.25-7.38 (m, 5H), 4.63 (m, 1H), 4.19 (q, J=7 Hz, 2H), 4.07 (s, 2H) 3.46-3.38 (m, 1H) 3.33-3.26 (m, 1H), 2.43-35 (m, 1H), 2.09-1.99 (m, 1H), 1.50 (d, J=7.4 Hz, 3H), 1.43 (s, 9H), 1.29 (t, J=7.0 Hz, 3H).

(3R,4S)-4-((S)-1-Phenyl-ethylamino)-piperidine-1,3-dicarboxylic acid 1-tert-butyl ester 3-ethyl ester Sodium borohydride (1.43 g, 37.85 mmol) is dissolved in THF (100 mL) at −15° C. under $N_2$. TFA (10.7 mL, 0.14 mmol) is added dropwise over 20 min. 4-((S)-1-phenyl-ethylamino)-5,6-dihydro-2H-pyridine-1,3-dicarboxylic acid 1-tert-butyl ester 3-ethyl ester (10.5 g, 28 mmol) is added over 10 min at −14 to −18° C. The resulting mixture is stirred for 60 min at 0° C. Ice-water (100 mL) is added carefully and the reaction mixture is stirred for 10 min at RT. A 3 M aq. NaOH solution is added to bring the mixture to pH 11. The reaction mixture is extracted with DCM (2×100 mL), the combined organic layers are washed with brine (2×100 mL), dried over $MgSO_4$ and the solvent is evaporated under reduced pressure. The resulting oil is purified by FC over 120 g of silica gel with heptane/EtOAc system (1:0 to 4:1) as eluent to give the title product as a yellowish oil (9.5 g). The title compound is contaminated by ~10% of the corresponding (3S,4R)-isomer. LC-MS method A: $t_R$=0.71 min; $[M+H]^+$=377.33. $^1H$ NMR (400 MHz, $CDCl_3$) δ: 7.31-7.41 (m, 5H), 4.14-4.27 (m, 3H), 4.02 (q, J=6.6 Hz, 1H), 3.74-3.85 (m, 3H), 3.00-3.10 (m, 2H), 2.89-2.94 (m, 2H), 1.88 (m, 1H), 1.60-1.65 (m, 1H), 1.42-1.46 (m, 11H), 1.28-1.38 (m, 3H).

(3R,4S)-4-Amino-piperidine-1,3-dicarboxylic acid 1-tert-butyl ester 3-ethyl ester A solution of (3R,4S)-4-((S)-1-phenyl-ethylamino)-piperidine-1,3-dicarboxylic acid 1-tert-butyl ester 3-ethyl ester (9.6 g, 25.5 mmol) in MeOH (250 mL) is added to a suspension of $Pd(OH)_2$ 20% on activated charcoal (1 g) under $H_2$. The mixture is stirred for 18 h at RT. The suspension is filtered through Celite and the filtrate is concentrated under vacuo to obtain the title product as a slightly yellow oil (5.65 g). The title compound contains ~10% of the corresponding (3S,4R)-isomer. LC-MS method A: $t_R$=0.54 min; $[M+H]^+$=273.26. $^1H$ NMR (400 MHz, $CDCl_3$) δ: 4.56-4.65 (m, 1H), 4.40-4.65 (m, 2H), 4.04-4.30 (m, 3H), 3.59-3.72 (m, 1H), 3.01-3.21 (m, 2H), 2.51-2.68 (m, 2H), 1.98-2.11 (m, 1H), 1.73-1.77 (m, 1H), 1.46 (m, 8H), 1.26-1.39 (m, 3H).

(3R,4S)-4-{[5-(2,4-Difluoro-phenyl)-isoxazole-3-carbonyl]-amino}-piperidine-1,3-dicarboxylic acid 1-tert-butyl ester 3-ethyl ester To a solution of (3R,4S)-4-amino-piperidine-1,3-dicarboxylic acid 1-tert-butyl ester 3-ethyl ester (12.15 g, 27.2 mmol) in DCM (200 mL) at RT is added 5-(2,4-difluoro-phenyl)isoxazole-3-carboxylic acid (6.1 g, 26.3 mmol). TEA (15.2 mL, 109 mmol) is then added followed by T3P 50% in DCM (32.4 mL, 54.4 mmol). The reaction mixture is stirred for 24 h at RT. The reaction mixture is washed twice with aq. sat. $NaHCO_3$ (2×100 mL). The organic layer is dried over $MgSO_4$ and evaporated. The crude residue is purified by FC over 100 g of silica gel with heptane/EtOAc system (1:0 to 85:15) as eluent to yield the title compound as a white powder (10.25 g); The title compound contains ~10% of the corresponding (3S,4R)-isomer; LC-MS method A: $t_R$=1.15 min; $[M+H]^+$=480.1. $^1H$ NMR (400 MHz, $CDCl_3$) δ: 7.96-8.00 (m, 1H), 7.81-7.89 (m, 1H), 6.98-7.13 (m, 2H), 4.54-4.62 (m, 1H), 4.42-4.52 (m, 1H), 3.97-4.28 (m, 2H), 3.14-3.21 (m, 1H), 2.88-3.08 (m, 2H), 2.03-2.18 (m, 1H), 1.78-1.87 (m, 1H), 1.58 (s, 2H), 1.48-1.52 (m, 9H), 1.28-1.37 (m, 3H).

(3S,4S)-4-{[5-(2,4-Difluoro-phenyl)-isoxazole-3-carbonyl]-amino}-piperidine-1,3-dicarboxylic acid 1-tert-butyl ester 3-ethyl ester Sodium ethoxide (3.225 g, 45 mmol) is added to a solution of (3R,4S)-4-{[5-(2,4-difluoro-phenyl)-isoxazole- 3-carbonyl]-amino}-piperidine-1,3-dicarboxylic acid 1-tert-butyl ester 3-ethyl ester (3.6 g, 7.5 mmol) in a mixture of EtOH (40 mL) and EtOAc (20 mL). The mixture is stirred at RT for 1 day. The reaction mixture is treated with aq. sat. NH$_4$Cl (25 mL). DCM (50 mL) is added. The organic phase is separated and the aq. layer is extracted thrice with DCM (3×50 mL). The combined organic layers are dried over MgSO$_4$, filtered and concentrated. The crude residue is purified by prep. LC-MS with basic conditions (method B). The title compound is obtained as a colourless powder (1.91 g), it contains ~10% of the corresponding (3S,4R)-isomer.

The enantiomerically pure title compound is obtained by chiral preparative SFC of the mixture of (3S,4S)-4-{[5-(2,4-Difluoro-phenyl)-isoxazole-3-carbonyl]-amino}-piperidine-1,3-dicarboxylic acid 1-tert-butyl ester 3-ethyl ester containing ~10% of (3R,4R)-4-{[5-(2,4-Difluoro-phenyl)-isoxazole-3-carbonyl]-amino}-piperidine-1,3-dicarboxylic acid 1-tert-butyl ester 3-ethyl ester using a column ChiralPak IC, 5 μm, 30×250 mm; with a mixture of A (80% CO$_2$) and B (50% DCM, 20% MeOH, 0.1% DEA) as eluent and a flow of 160 mL/min. Chiral HPLC: $t_R$=3.29 min. LC-MS method A: $t_R$=1.06 min; [M+H]$^+$=480.08. $^1$H NMR (400 MHz, CDCl$_3$) δ: 8.90-8.94 (m, 1H), 8.04-8.10 (m, 1H), 7.57-7.62 (m, 1H), 7.31-7.38 (m, 1H), 7.11-7.16 (m, 1H), 4.23-4.32 (m, 1H), 4.05-4.13 (m, 1H), 4.03 (q, J=7.1 Hz, 2H), 3.92-3.97 (m, 1H), 2.80-3.06 (m, 2H), 2.61-2.69 (m, 1H), 1.77-1.81 (m, 1H), 1.48-1.58 (m, 1H), 1.40-1.46 (m, 9H), 1.08 (t, J=7.1 Hz, 3H).

(3S,4S)-4-{[5-(2,4-Difluoro-phenyl)-isoxazole-3-carbonyl]-amino}-piperidine-1,3-dicarboxylic acid 1-tert-butyl ester (3S,4S)-4-{[5-(2,4-Difluoro-phenyl)-isoxazole-3-carbonyl]-amino}-piperidine-1,3-dicarboxylic acid 1-tert-butyl ester 3-ethyl ester (4.98 g, 10.7 mmol) is dissolved in THF (80 mL). Aq. 1M NaOH solution (20 mL, 20 mmol) is then added and the mixture stirred at RT for 3 h. The reaction mixture is acidified to around pH=3 with 2M aq. HCl solution (10 mL) and extracted thrice with DCM (3×50 mL). The combined organic phases are dried over MgSO$_4$, filtered and concentrated. The title compound is obtained as a white powder (4.56 g); LC-MS method A $t_R$=0.99 min; [M+H]$^+$= 452.33. $^1$H NMR (400 MHz, DMSO-d6) δ: 12.51 (s, 1H), 8.90 (d, J=8.8 Hz, 1H), 8.07 (td, J$_1$=8.6 Hz, J$_2$=6.4 Hz, 1H), 7.60 (m, 1H), 7.34 (td, J$_1$=8.5 Hz, J$_2$=2.2 Hz, 1H), 7.15 (d, J=2.9 Hz, 1H), 4.26 (m, 1H), 4.04-4.17 (m, 1H), 3.92-3.95 (m, 1H), 2.79-3.01 (m, 2H), 2.60 (td, J$_1$=11.0 Hz, J$_2$=4.0 Hz, 1H), 1.75-1.82 (m, 1H), 1.36-1.54 (m, 10H).

(3S,4S)-4-{[5-(2,4-Difluoro-phenyl)-isoxazole-3-carbonyl]-amino}-3-(1-pyrimidin-2-yl-cyclopropylcarbamoyl)-piperidine-1-carboxylic acid tert-butyl ester To a solution of (3S,4S)-4-{[5-(2,4-difluoro-phenyl)-isoxazole-3-carbonyl]-amino}-piperidine-1,3-dicarboxylic acid 1-tert-butyl ester (400 mg, 0.88 mmol) in DMF (15 mL) are added 1-(pyrimidin-2-yl)cyclopropan-1-amine hydrochloride (171 mg, 0.975 mmol), DIPEA (0.805 mL, 4.61 mmol) and HATU (404 mg, 1.06 mmol). The reaction mixture is stirred at RT for 4 h. The volatiles are evaporated and the crude mixture is purified by prep. LC-MS with basic conditions (Method B) to give the title compound (419 mg); LC-MS method A $t_R$=0.95 min; [M+H]$^+$=568.97. $^1$H NMR (500 MHz, DMSO-d6) δ: 8.62 (d, J=8.6 Hz, 1H), 8.53 (d, J=4.8 Hz, 3H), 8.08 (d, J=6.4 Hz, 1H), 7.34 (d, J=2.4 Hz, 1H), 7.19-7.21 (m, 1H), 7.17 (d, J=3.0 Hz, 1H), 3.92-4.1 (m, 2H) 3.63 (m, 1H), 3.35-3.45 (m, 1H), 3.15-3.26 (m, 2H), 2.75-2.92 (m, 1H), 1.42-154 (m, 4H), 1.22-1.44 (m, 11H).

(3S,4S)-4-{[5-(2,4-Difluoro-phenyl)-isoxazole-3-carbonyl]-amino}-piperidine-3-carboxylic acid (1-pyrimidin-2-yl-cyclopropyl)-amide hydrochloride (3S,4S)-4-{[5-(2,4-Difluoro-phenyl)-isoxazole-3-carbonyl]-amino}-3-(1-pyrimidin-2-yl-cyclopropylcarbamoyl)-piperidine-1-carboxylic acid tert-butyl ester (419 mg, 0.74 mmol) is dissolved in dioxane (10 mL). HCl in dioxane 4M (5 mL, 20 mmol) is added dropwise. The mixture is stirred at RT for 1 h. The solvents are evaporated and the residue is dried on HV to deliver the title crude compound as a white powder (365 mg). LC-MS method A: $t_R$=0.64 min; [M+H]$^+$= 469.17. $^1$H NMR (400 MHz, DMSO-d6) δ: 9.38-9.41 (m, 1H), 9.27-9.29 (m, 1H), 9.00 (d, J=8.5 Hz, 1H), 8.93 (s, 1H), 8.57 (d, J=4.8 Hz, 2H), 8.06 (q, J=7.8 Hz, 1H), 7.59 (t, J=10.5 Hz, 1H), 7.31-7.39 (m, 2H), 7.25 (t, J=4.8 Hz, 1H), 4.27 (d, J=9.8 Hz, 1H), 3.34 (m, 2H), 3.07-3.20 (m, 3H), 2.03 (m, 1H), 1.86-1.89 (m, 1H), 1.51 (m, 1H), 1.37-1.41 (m, 1H), 1.03-1.11 (m, 2H).

(3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide To a suspension of (3S,4S)-4-{[5-(2,4-difluoro-phenyl)-isoxazole-3-carbonyl]-amino}-piperidine-3-carboxylic acid methyl ester hydrochloride (200 mg, 0.396 mmol) in DCM (20 mL) at RT is added cyclopropanecarboxaldehyde (0.03 mL, 0.396 mmol) followed by DIPEA (0.2 mL, 1.2 mmol) and sodium triacetoxyborohydride (221 mg, 1 mmol). The reaction mixture is stirred for 2 h at RT. The reaction mixture is treated with aq. sat. NaHCO$_3$ twice (50 mL). The organic phase is dried over MgSO$_4$ and evaporated. The crude residue is purified by prep. LC-MS under basic conditions (method B) to yield the title compound as a colourless solid (148 mg); Chiral HPLC: $t_R$=2.42 min; LC-MS method A: $t_R$=0.69 min; [M+H]$^+$=523.04. $^1$H NMR (400 MHz, DMSO-d6) δ: 8.57 (d, J=8.4 Hz, 1H), 8.51 (d, J=4.7 Hz, 2H), 8.47 (s, 1H), 8.08 (dd, J$_1$=8.2 Hz, J$_2$=15.7 Hz, 1H), 7.59 (t, J=9.8 Hz, 1H), 7.34 (t, J=8.3 Hz, 1H), 7.12-7.23 (m, 2H), 3.95-4.06 (m, 1H), 3.14 (d, J=10.0 Hz, 1H), 2.99 (d, J=10.3 Hz, 1H), 2.72 (t, J=9.3 Hz, 1H), 2.18-2.27 (m, 2H), 2.12 (t, J=11.4 Hz, 1H), 2.01 (t, J=11.5 Hz, 1H), 1.85 (d, J=11.0 Hz. 1H), 1.54-1.66 (m, 1H), 1.45-1.51 (m, 1H), 1.31-1.41 (m, 1H), 1.04-1.16 (m, 2H), 0.79-0.90 (m, 1H), 0.49 (d, J=7.6 Hz, 2H), 0.10 (d, J=4.1 Hz, 2H).

II. BIOLOGICAL ASSAYS

In Vitro Assay

The antagonistic effect of COMPOUND on the CXCR7 receptor is determined in accordance with the following experimental method.

The assay is using the Tango CXCR7-bla U2OS cell line from invitrogen. These cells contain the human chemokine receptor CXCR7 linked to a TEV protease site and a Gal4-VP16 transcription factor stably integrated into the Tango GPCR-bla U2OS parental cell line. This parental cell line stably express a beta-arrestin/TEV protease fusion protein and the beta-lactamase reporter gene under the control of a UAS response element.

Upon ligand binding and receptor activation, the protease-tagged beta-arrestin molecule is recruited to CXCR7 which is linked at the C-terminus by a protease cleavage site to a transcription factor. The protease cleaves the transcription factor from CXCR7, which translocates to the nucleus and activates the expression of beta-lactamase. A FRET-enabled substrate allows to detect beta-lactamase expression.

Tango CXCR7-bla U2OS cells are detached from culture dishes with 0.05% trypsin-EDTA and collected in growing medium (McCoy's 5A 90% (v/v), dialyzed FCS 10% (v/v), 0.1 mM NEAA, 25 mM HEPES (pH 7.3), 1 mM sodium pyruvate, P/S 1% (v/v) 50 µg/mL Hygromycin, 100 µg/mL Geneticin, 200 µg/mL Zeocin), spinned down and resuspended in assay medium (McCoy's 5A 90% (v/v), dialyzed FCS 1% (v/v), 0.1 mM NEAA, 25 mM HEPES (pH 7.3), P/S 1% (v/v)). 10,000 cells per well (in 30 µL) are seeded in a 384 well plate (black-walled, clear bottom). The plate is incubated at 37° C./5% $CO_2$ for 24 hours. Test compounds are dissolved to 10 mM in DMSO and serially diluted in DMSO to 500× of the final concentration for dose response curves. Compounds are then diluted 1:100 in assay medium to 5× of the final concentration. 10 µL/well of diluted compounds are added to the assay plate and incubated for 15 minutes at 37° C. Thereafter CXCL12/SDF1-α is diluted in assay medium to 5× of the final concentration (its EC80 value for receptor activation) and 10 µl/well are added to the assay plate. The agonist leads to activation of the receptor and therefore to b-arrestin recruitment. Compounds acting as antagonists reduce this activation. The plate is incubated for 22 h at 37° C. 10 µL/well of detection reagent (Live-BLAzer™-FRET B/G (CCF4-AM) substrate) is transferred to the assay plate and the plate is incubated for 2 hours at room temperature protected from light. Fluorescent counts are determined (Scan1: Ex 409/20 nm, Em 460/30 nm, Scan 2: Ex 409/20 nm, Em 530/30 nm). The calculated emission ratio is used for $IC_{50}$ determination. The calculated $IC_{50}$ values may fluctuate depending on the daily cellular assay performance. Fluctuations of this kind are known to those skilled in the art. Average $IC_{50}$ values from several measurements are given as geometric mean values. The compound of Reference Example 1 was tested to have an $IC_{50}$ of 3 nM in this assay.

III. EXAMPLES

Example 1

(3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide in Crystalline Form 1

1 mL of MeOH is added to 10 mg of COMPOUND (e.g. as obtained from Reference Example 1) in a standard HPLC vial, the suspension is dissolved by heating to 65° C. with a ramp of 0.1° C./min while stirring with a magnetic bar at 500 rpm using a Crystal 16 device (Crystallization Systems, NL). The solution is then cooled down to 20° C. with a ramp of 0.1° C./min. The obtained solid is COMPOUND in crystalline form 1.

Alternatively, 1 mL of MeOH/MeCN 3/1 is added to 20 mg of COMPOUND (e.g. as obtained from Reference Example 1) in a standard HPLC vial, the suspension is dissolved by heating to 65° C. with a ramp of 0.1° C./min while stirring with a magnetic bar at 500 rpm using a Crystal 16 device (Crystallization Systems, NL). The solution is then cooled down to 20° C. with a ramp of 0.1° C./min. The obtained solid is COMPOUND in crystalline form 1.

| | |
|---|---|
| XRPD method 1 | Form 1, FIG. 1 |
| Tm (peak value, DSC in pierced pan 10° C./min) | 259° C. |
| 1H-NMR | conforms |
| Moisture sorption | Slightly hygroscopic |

Example 2

(3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide in Crystalline Form 2

100 mg of COMPOUND in Form 1 are suspended in 1 mL DCM and gently stirred at RT with a magnetic stirring bar placed in 4 mL glass vial. After 1 week, the solid is isolated and the solid is COMPOUND in crystalline form 2.

Alternatively, 1 mL of MeOH/MeCN 3/1 is added to 10 mg of COMPOUND (e.g. as obtained from Reference Example 1) in a standard HPLC vial, the suspension is dissolved by heating to 40° C. with a ramp of 0.1° C./min while stirring with a magnetic bar at 500 rpm using a Crystal 16 device (Crystallization Systems, NL). The solution is then cooled down to 20° C. with a ramp of 0.1° C./min. The obtained solid is COMPOUND in crystalline form 2.

| | |
|---|---|
| XRPD method 1 | Form 2, FIG. 2 |
| Moisture sorption | Sorption of 6.9% at 95% RH |

Example 3

(3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide in Crystalline Form 3

50 mg of COMPOUND in Form 2 are suspended in 0.4 mL water in a 4 mL glass vial and gently shaken at RT on an orbital shaker. After 1 day, the obtained solid, when measured in wet state, is COMPOUND in crystalline form 3. Crystalline form 3 is a dihydrate.

| | |
|---|---|
| XRPD method 2 | Form 3, FIG. 3 |

Example 4

(3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide in Crystalline Form 4

10 mg of COMPOUND are dissolved in 3 mL THF in a 4 mL glass vial and is allowed to evaporate at ambient conditions. After complete evaporation of the solid (after 3 days), the solid measured is COMPOUND in crystalline form 4.

Alternatively, 10 mg of COMPOUND in Form 2 are suspended in 0.02 mL THF/$H_2O$ 9/1 and the vial is allowed

The invention claimed is:

1. A crystalline form of a compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide

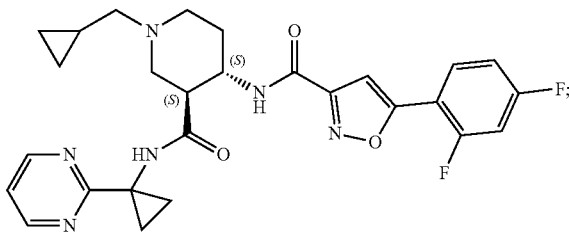

having an X-ray powder diffraction pattern wherein:
  a. peaks are present in the X-ray powder diffraction pattern at the following angles of refraction 2θ: 3.6°, 8.2°, and 18.3°; corresponding to crystalline form 1; or
  b. peaks are present in the X-ray powder diffraction pattern at the following angles of refraction 2θ: 6.7°, 8.5°, and 10.9°; corresponding to crystalline form 2; or
  c. peaks are present in the X-ray powder diffraction pattern at the following angles of refraction 2θ: 8.2° 17.9°, and 21.0°; corresponding to crystalline form 3;

wherein said X-ray powder diffraction pattern is obtained from combined Cu Kα1 and Kα2 radiation, without Kα2 stripping; and the accuracy of the 2θ values is in the range of 2θ+/−0.2°.

2. The crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 1, wherein peaks are present in the X-ray powder diffraction pattern at the following angles of refraction 2θ: 3.6°, 7.2°, 8.2°, 8.7°, and 18.3°.

3. The crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 1, peaks are present in the X-ray powder diffraction pattern at the following angles of refraction 2θ: 3.6°, 7.2°, 8.2°, 8.7°, 9.1°, 10.8°, 13.9°, 17.0°, 17.5°, and 18.3°.

4. The crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 2, which essentially shows the X-ray powder diffraction pattern as depicted in FIG. 1.

5. The crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 2, which has an endothermal event at about 259° C. as determined by differential scanning calorimetry.

6. The crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 2, wherein said crystalline form is an anhydrate.

7. The crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 2, corresponding to crystalline form 1, obtainable by:
  a) mixing 10 mg of (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide with 1 mL of methanol, or mixing 20 mg of (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide with 1 mL of an about 3 to 1 mixture of methanol and acetonitrile;
  b) dissolving (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide by heating to about 65° C. with a ramp of 0.1° C./min;
  c) cooling the mixture to about 20° C. by using a ramp of 0.1° C./min; and
  d) filtering and drying the product.

8. The crystalline form of the compound ((3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 1, wherein:
  a. peaks are present in the X-ray powder diffraction pattern at the following angles of refraction 2θ: 6.7°, 8.5°, 10.9°, 13.2°, and 14.5°; or
  b. peaks are present in the X-ray powder diffraction pattern at the following angles of refraction 2θ: 6.8°, 8.2°, 14.1°, 17.9°, and 21.0°.

9. The crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 8, wherein:
  a. peaks are present in the X-ray powder diffraction pattern at the following angles of refraction 2θ: 6.7°, 8.5°, 10.9°, 13.2°, and 14.5°; which essentially shows the X-ray powder diffraction pattern as depicted in FIG. 2; or
  b. peaks are present in the X-ray powder diffraction pattern at the following angles of refraction 2θ: 6.8°, 8.2°, 14.1°, 17.9°, and 21.0°; which essentially shows the X-ray powder diffraction pattern as depicted in FIG. 3.

10. The crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 8, wherein said crystalline form is an anhydrate and peaks are present in the X-ray powder diffraction pattern at the following angles of refraction 2θ: 6.7°, 8.5°, 10.9°, 13.2°, and 14.5°.

11. The crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 8, wherein said crystalline form is an anhydrate and peaks are present in the X-ray powder diffraction pattern at the following angles of refraction 2θ: 6.8°, 8.2°, 14.1°, 17.9°, and 21.0°.

12. A pharmaceutical composition comprising as active ingredient a crystalline form of the compound (3S,4S)-1-

Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 1, and at least one pharmaceutically acceptable carrier.

13. A pharmaceutical composition comprising the crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 3, and at least one pharmaceutically acceptable carrier material.

14. A method for the treatment of cancer comprising administering to a patient in need thereof a crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 1.

15. A method for the treatment of cancer comprising administering to a patient in need thereof a crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 3.

16. A method for treatment of cancer comprising administering to a patient an effective amount of a crystalline form of the compound (3S,4S)-1-Cyclopropylmethyl-4-{[5-(2,4-difluoro-phenyl)-isoxazole-3-carbonyl]-amino}-piperidine-3- carboxylic acid (1-pyrimidin-2-yl-cyclopropyl)-amide according to claim 10.

17. A pharmaceutical composition comprising as active ingredient a crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 10, and at least one pharmaceutically acceptable carrier.

18. A pharmaceutical composition comprising as active ingredient a crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 11, and at least one pharmaceutically acceptable carrier.

19. A method for treatment of cancer comprising administering to a patient an effective amount of a crystalline form of the compound (3S,4S)-1-Cyclopropylmethyl-4-{[5-(2,4-difluoro-phenyl)-isoxazole-3-carbonyl]-amino}-piperidine-3- carboxylic acid (1-pyrimidin-2-yl-cyclopropyl)-amide according to claim 11.

20. A method for treatment of cancer according to claim 14, wherein the cancer is selected from carcinomas, leukemia, sarcomas, lymphomas, myelomas, metastatic cancers, brain tumors, neuroblastomas, pancreatic cancer, lung and breast cancer, endometrial cancer, head and neck cancer, or ovarian cancer.

21. A method for treatment of autoimmune disorders which have an inflammatory component selected from inflammatory demyelinating diseases, multiple sclerosis (MS), Guillain Barré syndrome, rheumatoid arthritis (RA), inflammatory bowel disease (IBD), systemic lupus erythematosus (SLE), lupus nephritis, and auto-immune encephalomyelitis; comprising administering to a patient an effective amount of a crystalline form of the compound (3S,4S)-1-Cyclopropylmethyl-4-{[5-(2,4-difluoro-phenyl)-isoxazole-3-carbonyl]-amino}- piperidine-3-carboxylic acid (1-pyrimidin-2-yl-cyclopropyl)-amide according to claim 1.

22. A method for treatment of autoimmune disorders which have an inflammatory component selected from inflammatory demyelinating diseases, multiple sclerosis (MS), Guillain Barré syndrome, rheumatoid arthritis (RA), inflammatory bowel disease (IBD), systemic lupus erythematosus (SLE), lupus nephritis, and auto-immune encephalomyelitis; comprising administering to a patient an effective amount of a crystalline form of the compound (3S,4S)-1-Cyclopropylmethyl-4-{[5-(2,4-difluoro-phenyl)-isoxazole-3-carbonyl]-amino}- piperidine-3-carboxylic acid (1-pyrimidin-2-yl-cyclopropyl)-amide according to claim 3.

23. A method for treatment of autoimmune disorders which have an inflammatory component selected from inflammatory demyelinating diseases, multiple sclerosis (MS), Guillain Barré syndrome, rheumatoid arthritis (RA), inflammatory bowel disease (IBD), systemic lupus erythematosus (SLE), lupus nephritis, and auto-immune encephalomyelitis; comprising administering to a patient an effective amount of a crystalline form of the compound (3S,4S)-1-Cyclopropylmethyl-4-{[5-(2,4-difluoro-phenyl)-isoxazole-3-carbonyl]-amino}- piperidine-3-carboxylic acid (1-pyrimidin-2-yl-cyclopropyl)-amide according to claim 10.

24. A method for treatment of autoimmune disorders which have an inflammatory component selected from inflammatory demyelinating diseases, multiple sclerosis (MS), Guillain Barré syndrome, rheumatoid arthritis (RA), inflammatory bowel disease (IBD), systemic lupus erythematosus (SLE), lupus nephritis, and auto-immune encephalomyelitis; comprising administering to a patient an effective amount of a crystalline form of the compound (3S,4S)-1-Cyclopropylmethyl-4-{[5-(2,4-difluoro-phenyl)-isoxazole-3-carbonyl]-amino}- piperidine-3-carboxylic acid (1-pyrimidin-2-yl-cyclopropyl)-amide according to claim 11.

25. A method for treatment of inflammatory diseases selected from
    lung inflammatory diseases selected from asthma, chronic obstructive pulmonary disorder (COPD), and acute lung injury; and
    atherosclerosis;
comprising administering to a patient an effective amount of a crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 1.

26. A method for treatment of inflammatory diseases selected from
    lung inflammatory diseases selected from asthma, chronic obstructive pulmonary disorder (COPD), and acute lung injury; and
    atherosclerosis;
comprising administering to a patient an effective amount of a crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 3.

27. A method for treatment of inflammatory diseases selected from
    lung inflammatory diseases selected from asthma, chronic obstructive pulmonary disorder (COPD), and acute lung injury; and
    atherosclerosis;
comprising administering to a patient an effective amount of a crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 10.

28. A method for treatment of inflammatory diseases selected from
    lung inflammatory diseases selected from asthma, chronic obstructive pulmonary disorder (COPD), and acute lung injury; and
    atherosclerosis;

comprising administering to a patient an effective amount of a crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 11.

29. A method for treatment of fibrosis; comprising administering to a patient an effective amount of a crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 1.

30. A method for treatment of fibrosis; comprising administering to a patient an effective amount of a crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 3.

31. A method for treatment of fibrosis; comprising administering to a patient an effective amount of a crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 10.

32. A method for treatment of fibrosis; comprising administering to a patient an effective amount of a crystalline form of the compound (3S,4S)-1-Cyclopropylmethyl-4-{[5-(2,4-difluoro-phenyl)-isoxazole-3-carbonyl]-amino}-piperidine-3-carboxylic acid (1-pyrimidin-2-yl-cyclopropyl)-amide according to claim 11.

\* \* \* \* \*